United States Patent
Murata et al.

(10) Patent No.: US 12,295,394 B2
(45) Date of Patent: May 13, 2025

(54) WATER-SOLUBLE ADDITIVE COMPOSITION

(71) Applicants: SUMITOMO BAKELITE CO., LTD., Tokyo (JP); RESEARCH INSTITUTE OF INNOVATIVE TECHNOLOGY FOR THE EARTH, Kizugawa (JP)

(72) Inventors: Ryuichi Murata, Tokyo (JP); Yusuke Inoue, Tokyo (JP); Daisuke Fujiwara, Tokyo (JP); Kenya Tachibana, Tokyo (JP); Hiroyuki Miyauchi, Tokyo (JP)

(73) Assignees: SUMITOMO BAKELITE CO., LTD., Tokyo (JP); RESEARCH INSTITUTE OF INNOVATIVE TECHNOLOGY FOR THE EARTH, Kyoto (JP)

( * ) Notice: Subject to any disclaimer, the term of this patent is extended or adjusted under 35 U.S.C. 154(b) by 552 days.

(21) Appl. No.: 17/442,157

(22) PCT Filed: Mar. 23, 2020

(86) PCT No.: PCT/JP2020/012763
§ 371 (c)(1),
(2) Date: Sep. 23, 2021

(87) PCT Pub. No.: WO2020/196424
PCT Pub. Date: Oct. 1, 2020

(65) Prior Publication Data
US 2022/0175000 A1    Jun. 9, 2022

(30) Foreign Application Priority Data

Mar. 28, 2019 (JP) .................. 2019-064431
Mar. 28, 2019 (JP) .................. 2019-064432

(Continued)

(51) Int. Cl.
*A23L 27/20*    (2016.01)
*A23L 27/00*    (2016.01)
(Continued)

(52) U.S. Cl.
CPC ............. *A23L 27/204* (2016.08); *A23L 27/21* (2016.08); *A23L 27/88* (2016.08); *A23L 29/035* (2016.08);
(Continued)

(58) Field of Classification Search
CPC ...... A23L 27/204; A23L 27/88; A23L 33/105; A61K 2800/10; A61K 8/445; A61K 8/365
See application file for complete search history.

(56) References Cited

U.S. PATENT DOCUMENTS 5,637,293 A    6/1997   Honda
5,750,563 A    5/1998   Honda
(Continued)

FOREIGN PATENT DOCUMENTS

EP    3184626       6/2017
JP    45-039036     12/1970
(Continued)

OTHER PUBLICATIONS

Moh et al., KR 20110028745A, Abstract, Feb. 28, 2012.*
(Continued)

*Primary Examiner* — Jafar F Parsa
(74) *Attorney, Agent, or Firm* — Amin, Turocy & Watson, LLP

(57) ABSTRACT

There is provided a water-soluble additive composition including a cyclic carboxylic acid, the water-soluble additive composition satisfying at least one of the following Conditions 1 to 4: (Condition 1) component (A) the cyclic carboxylic acid, which is other than the following component (B1), and component (B1) one or more selected from
(Continued)

the group consisting of gallic acid and an ester thereof are included; (Condition 2) the total content of Na+ and NH4+ is equal to or more than 100 ppm and equal to or less than 5000 ppm with respect to the cyclic carboxylic acid; (Condition 3) the total inorganic ion content (excluding hydrogen ions and hydroxyl group ions) is equal to or more than 300 ppm and equal to or less than 5000 ppm with respect to the cyclic carboxylic acid; and (Condition 4) component (A) the cyclic carboxylic acid, which is other than the following component (B2), and component (B2) an amino acid are included.

8 Claims, 4 Drawing Sheets

(30) Foreign Application Priority Data

Mar. 29, 2019 (JP) .............................. 2019-066870
Mar. 29, 2019 (JP) .............................. 2019-066874
Mar. 29, 2019 (JP) .............................. 2019-066883

(51) Int. Cl.
    *A23L 27/21*    (2016.01)
    *A23L 29/00*    (2016.01)
    *A23L 29/212*   (2016.01)
    *A23L 29/262*   (2016.01)
    *A23L 33/14*    (2016.01)
    *A23L 33/175*   (2016.01)
    *C12P 7/42*     (2006.01)

(52) U.S. Cl.
    CPC ............ *A23L 29/065* (2016.08); *A23L 29/212* (2016.08); *A23L 29/262* (2016.08); *A23L 33/14* (2016.08); *A23L 33/175* (2016.08); *C12P 7/42* (2013.01)

(56) References Cited

U.S. PATENT DOCUMENTS

| | | | |
|---|---|---|---|
| 9,782,336 | B2 | 10/2017 | Haraya et al. |
| 2007/0248694 | A1* | 10/2007 | Subbiah .................. A61K 36/47 514/570 |
| 2017/0181947 | A1 | 6/2017 | Haraya et al. |
| 2021/0236444 | A1 | 8/2021 | Inoue et al. |

FOREIGN PATENT DOCUMENTS

| | | |
|---|---|---|
| JP | 05-238986 | 9/1993 |
| JP | 07-126135 | 5/1995 |
| JP | 08-092589 | 4/1996 |
| JP | 2004-035440 | 2/2004 |
| JP | 2007-238469 | 9/2007 |
| JP | 2009-215266 | 9/2009 |
| JP | 2013-155158 | 8/2013 |
| JP | 2014-031347 | 2/2014 |
| JP | 2017-088708 | 5/2017 |
| JP | 2018-150288 | 9/2018 |
| WO | 2016/039407 | 3/2016 |
| WO | 2019/044773 | 3/2019 |
| WO | 2020/040017 | 2/2020 |

OTHER PUBLICATIONS

International Search Report and Written Opinion for International Application No. PCT/JP2020/012763 mailed on Jun. 16, 2020, 12 pages.
Kubota, et al. "Increasing Diversity of the Bio-Based Chemicals Produced by Corynebacterium glutamicum", Kagaku To Seibutsu, 2017, vol. 55, No. 10, pp. 690-698.
Kallscheuer, et al. "Identification of the phd gene cluster responsible for phenylpropanoid utilization in Corynebacterium glutamicum", Appl Microbiol Biotechnol, 2016, vol. 100, pp. 1871-1881.
Lorenzo, et al. "Phenolic compounds of green tea: Health benefits and technological application in food", Asian Pacific Journal of Tropical Biomedicine, vol. 6, No. 8, Aug. 1, 2016, pp. 709-719.
Jeszka-Skowron, et al. "Determination of antioxidant activity, rutin, quercetin, phenolic acids and trace elements in tea infusions: Influence of citric acid addition on extraction of metals", Journal of Food Composition and Analysis, vol. 40, Jun. 1, 2015, pp. 70-77.
Okai, et al. "Production of protocatechuic acid by Corynebacterium glutamicum expressing chorismate-pyruvate lyase from *Escherichia coli*", Applied Microbiology and Biotechnology, vol. 100, No. 1, Sep. 21, 2015, pp. 135-145.
Kitade, et al. "Production of 4-Hydroxybenzoic Acid by an Aerobic Growth-Arrested Bioprocess Using Metabolically Engineered Corynebacterium glutamicum", Applied and Environmental Microbiology, vol. 84, No., 6, Mar. 15, 2018.
Gutierrez-Larrainzar, et al. "Evaluation of antimicrobial and antioxidant activities of natural phenolic compounds against foodborne pathogens and spoilage bacteria", Food Control, vol. 26, No. 2, Aug. 1, 2012, pp. 555-563.
Lima, et al. "Antimicrobial and enhancement of the antibiotic activity by phenolic compounds: Gallic acid, caffeic acid and pyrogallol", Microbial Pathogenesis, vol. 99, Aug. 3, 2016, pp. 56-61.
Borges, et al. "Antibacterial Activity and Mode of Action of Ferulic and Gallic Acids Against Pathogenic Bacteria", Microbial Drug Resistance, vol. 19, No. 4, Aug. 1, 2013, pp. 256-265.
Jeszka-Skowron, et al. "Determination of antioxidant activity, rutin, quercetin, phenolic acids and trace elements in tea infusions: Influence of citric acid addition on extraction of metals", Journal of Food Composition and Analysis, 2015, vol. 40, pp. 70-77.
Toda, et al. "Antibacterial and anti-hemolysin activities of tea catechins and their structural relatives", Nihon Journal of Microbiology, vol. 45, No. 2, pp. 561-566.

* cited by examiner

WATER-SOLUBLE ADDITIVE COMPOSITION

TECHNICAL FIELD

The present invention relates to a water-soluble additive composition.

BACKGROUND ART

Regarding a technology related to a composition having a cyclic carboxylic acid incorporated therein, those described in Patent Documents 6 and 7 may be mentioned.

Patent Document 6 (Japanese Unexamined Patent Publication No. 2014-31347) describes a composition including a cyclic hydroxy acid having a specific structure or a derivative thereof and a sterol ester. According to the same patent document, such a composition can provide a composition having an excellent free radical scavenging effect and also having excellent characteristics in terms of irritation, usability, odor, and storage stability, and it is considered that aging phenomena such as wrinkle formation, loss of skin elasticity, and hair loss can be prevented or ameliorated by this composition.

In Patent Document 7 (WO 2016/039407), a composition including an acylproline having a particular structure or a salt thereof and a pyrrolidone carboxylic acid zinc salt is described as a technology for providing a composition having a peculiar odor of acylproline or a salt thereof at a reduced level and having a moist feeling and excellent stability, and it is also described that such a composition may include a hydroxycarboxylic acid.

RELATED DOCUMENT

Patent Document

[Patent Document 1] Japanese Unexamined Patent Publication No. 2004-35440
[Patent Document 2] Japanese Unexamined Patent Publication No. 2013-155158
[Patent Document 3] Japanese Unexamined Patent Publication No. 2009-215266
[Patent Document 4] Japanese Unexamined Patent Publication No. 7-126135
[Patent Document 5] Japanese Unexamined Patent Publication No. 2018-150288
[Patent Document 6] Japanese Unexamined Patent Publication No. 2014-31347
[Patent Document 7] WO 2016/039407
[Patent Document 8] Japanese Unexamined Patent Publication No. 2007-238469
[Patent Document 9] Japanese Unexamined Patent Publication No. 8-92589

SUMMARY OF THE INVENTION

Technical Problem

The present invention provides a novel composition including a cyclic carboxylic acid.

Solution to Problem

According to the present invention, there is provided a water-soluble additive composition including a cyclic carboxylic acid, in which the water-soluble additive composition satisfies at least one of the following Conditions 1 to 4:

(Condition 1) the following components (A) and (B1) are included:
(A) the cyclic carboxylic acid, which is other than the following component (B1), and
(B1) one or more selected from the group consisting of gallic acid and an ester thereof;
(Condition 2) a total content of $Na^+$ and $NH_4^+$ is equal to or more than 100 ppm and equal to or less than 5000 ppm with respect to the cyclic carboxylic acid;
(Condition 3) a total inorganic ion content (excluding hydrogen ions and hydroxyl group ions) is equal to or more than 300 ppm and equal to or less than 5000 ppm with respect to the cyclic carboxylic acid; and
(Condition 4) the following components (A) and (B2) are included:
(A) the above-described cyclic carboxylic acid, which is other than the following component (B2), and
(B2) an amino acid.

According to the present invention,
there is provided a food or a flavor, which contains at least one of a cyclic compound derived from a plant-derived saccharide and a microorganism and a derivative of the cyclic compound.

According to the present invention,
there is provided a food additive containing at least one of a cyclic compound derived from a plant-derived saccharide and a microorganism and a derivative of the cyclic compound.

According to the present invention,
there is provided a method for producing a cyclic compound or a derivative thereof, which is used as a food, a food additive, or a flavor, the method including:
preparing a culture liquid including a plant-derived saccharide and a microorganism so as to produce at least one of the cyclic compound and a derivative thereof;
concentrating the culture liquid to obtain a concentrated liquid; and
collecting at least one of the cyclic compound and a derivative thereof from the concentrated liquid by a crystallization method, a precipitation method, an extraction method, a sublimation purification method, or a distillation method.

Advantageous Effects of Invention

According to the present invention, a novel composition including a cyclic carboxylic acid may be provided.

DESCRIPTION OF EMBODIMENTS

Figure 1:
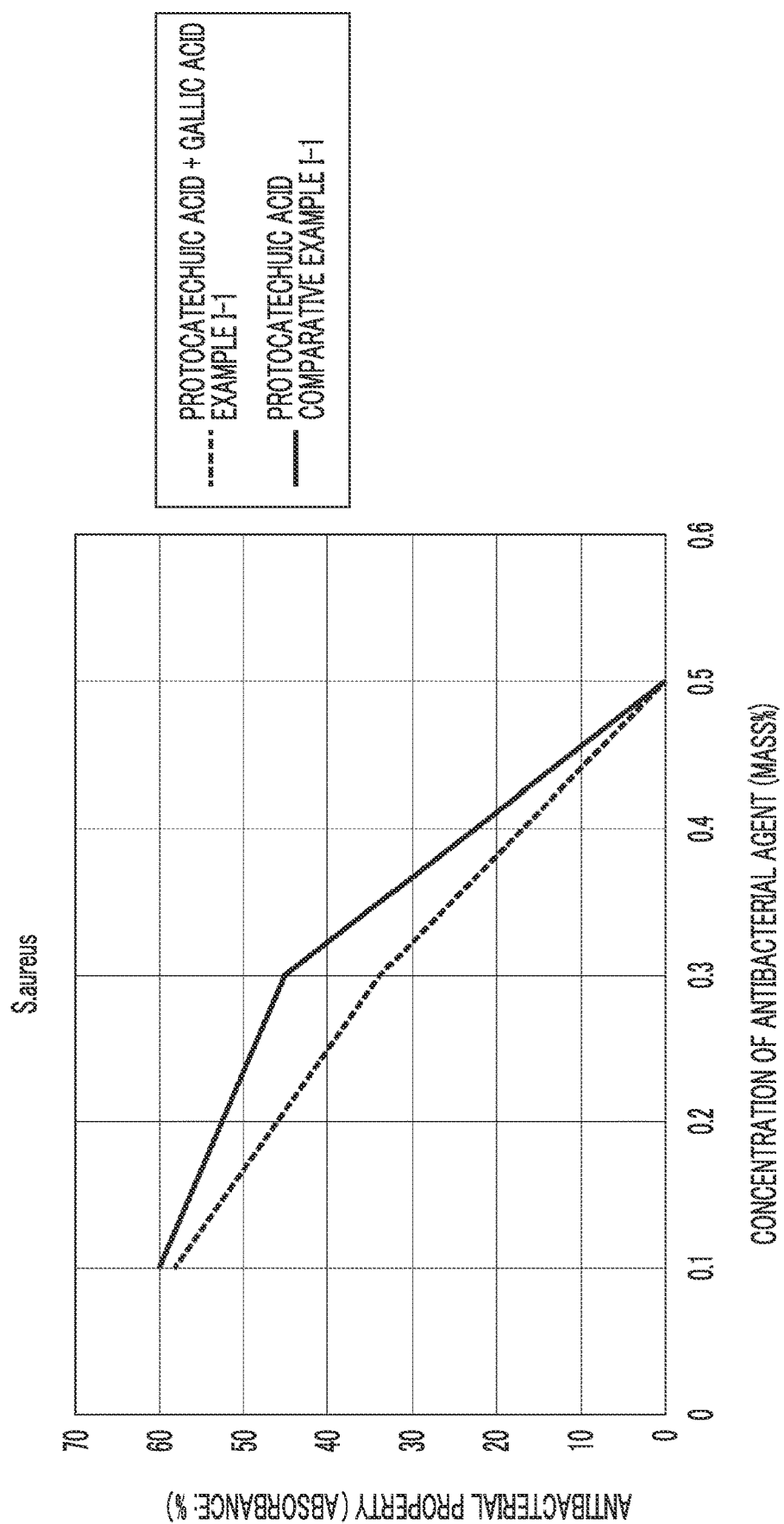
FIG. 1 is a diagram showing evaluation results for an antibacterial agent composition.

Hereinafter, embodiments of the present invention will be described with reference to specific examples. According to embodiments, the composition can include each of the components singly or in combination of two or more kinds thereof. Furthermore, the symbol "~" representing a numerical value range represents equal to or more than and equal to or less than the range and includes all the values at both ends of the range.

First Embodiment

The present embodiment relates to an antibacterial agent composition.

Technologies related to a composition having an antibacterial component incorporated therein include those described in Patent Documents 1 to 3.

In Patent Document 1 (Japanese Unexamined Patent Publication No. 2004-35440), a dullness inhibitor containing a specific melanin production inhibitor, a specific fibroblast growth promoter, and a specific blood circulation promoter is described, and it is described that an antibacterial agent such as shikimic acid may be further used in combination as an additive.

In Patent Document 2 (Japanese Unexamined Patent Publication No. 2013-155158), an antibacterial agent composition against one or more selected from the group consisting of the causative bacteria of acne vulgaris and the causative bacteria of dental caries, the antibacterial agent composition containing an onion outer skin extract, is described, and specifically, it is described that an antibacterial agent composition including respectively specific amounts of quercetin, quercetin-4'-glucoside, and protocatechuic acid was obtained.

In Patent Document 3 (Japanese Unexamined Patent Publication No. 2009-215266), a melanin production inhibitor containing one kind or two or more kinds of compounds selected from shikimic acid and salts thereof as active ingredients, and regarding the type of usage of such an agent, it is described that the use as a chelating agent or an antibacterial agent and the use for hair are excluded.

Furthermore, although the technical field is different, there is a composition described in Patent Document 4 as a composition including polyphenol.

Patent Document 4 (Japanese Unexamined Patent Publication No. 7-126135) describes an external medicine for skin obtained by adding at least one of an alcohol and/or a polyphenol to an external medicine including kojic acid and/or a derivative thereof and an ultraviolet absorber, and a large number of external medicines for skin including gallic acid, a gallic acid ester, and shikimic acid as the polyphenol are listed as examples.

The present inventors examined the technologies respectively described in the above-mentioned patent documents, and it was found that there is room for improvements in terms of improving antibacterial characteristics.

Thus, the present embodiment provides a composition having excellent antibacterial characteristics.

According to the present embodiment,
there is provided an antibacterial agent composition including the following components (A) and (B1):
(A) a cyclic carboxylic acid (excluding the following component (B1)), and
(B1) one or more selected from the group consisting of gallic acid and an ester thereof;

Furthermore, according to the present embodiment, for example, daily necessities or cosmetics, in which the antibacterial agent composition according to the above-mentioned present embodiment is incorporated, can be obtained.

According to the present embodiment, a composition having excellent antibacterial characteristics can be provided.

Hereinafter, embodiments will be described more specifically. According to the present embodiment, the composition can include each of the components singly or in combination of two or more kinds thereof.

According to the present embodiment, the antibacterial agent composition includes the following components (A) and (B1):
(A) a cyclic carboxylic acid (excluding the following component (B1)), and
(B1) one or more selected from the group consisting of gallic acid and an ester thereof;

(Component (A))

Component (A) is a cyclic carboxylic acid and is a component other than component (B1) that will be described later.

Specific examples of the component (A) include a cyclic carboxylic acid having one or two or more hydroxy groups, and a cyclic carboxylic acid having one or two or more amino groups, and a preferred example is a cyclic polyhydroxycarboxylic acid having two or more hydroxy groups.

Examples of the cyclic carboxylic acid include benzoic acid.

Examples of the cyclic carboxylic acid having a hydroxy group include an aromatic hydroxycarboxylic acid and an alicyclic hydroxycarboxylic acid.

Examples of the aromatic hydroxycarboxylic acid include hydroxybenzoic acids such as salicylic acid and 4-hydroxybenzoic acid, monohydroxybenzoic acids such as hydroxy (methyl)benzoic acid and hydroxy(methoxy)benzoic acid, and derivatives thereof;

dihydroxybenzoic acids, such as dihydroxybenzoic acids such as protocatechuic acid and gentisic acid, dihydroxy (methyl)benzoic acids such as orsellinic acid, and derivatives thereof; and monohydroxycinnamic acids such as ferulic acid, and derivatives thereof.

Examples of the alicyclic hydroxycarboxylic acid include shikimic acid and quinic acid.

The cyclic carboxylic acid having a hydroxy group preferably has two or more hydroxy groups.

Furthermore, examples of the cyclic carboxylic acid having an amino group include monoaminobenzoic acids such as 4-aminobenzoic acid, derivatives thereof, and other aromatic aminocarboxylic acids; and alicyclic aminocarboxylic acids.

From the viewpoint of enhancing the antibacterial characteristics of the antibacterial agent composition, the component (A) is preferably one or more selected from the group consisting of protocatechuic acid, shikimic acid, 4-hydroxybenzoic acid, 4-aminobenzoic acid, and ferulic acid; and more preferably one or more selected from the group consisting of protocatechuic acid and shikimic acid.

A content of the component (A) in the antibacterial agent composition may be, for example, equal to or more than 50% by mass with respect to the total amount of the antibacterial agent composition, from the viewpoint of enhancing the antibacterial characteristics, and the content is preferably equal to or more than 80% by mass, more preferably equal to or more than 90% by mass, even more preferably equal to or more than 95% by mass, and still more preferably equal to or more than 98% by mass.

From a similar point of view, the content of the component (A) in the antibacterial agent composition is less than 100% by mass with respect to the total amount of the antibacterial agent composition and is preferably equal to or less than 99.999% by mass, more preferably equal to or less than 99.990% by mass, even more preferably equal to or less than 99% by mass, and still more preferably equal to or less than 98% by mass.

(Component (B1))

Component (B1) is one or more selected from the group consisting of gallic acid and an ester thereof. Examples of the gallic acid ester include esters of linear alkyls having equal to or more than 1 and equal to or fewer than 20 carbon atoms, such as methyl gallate, ethyl gallate, propyl gallate, butyl gallate, pentyl gallate, hexyl gallate, heptyl gallate, octyl gallate, nonyl gallate, decyl gallate, lauryl gallate, and stearyl gallate.

From the viewpoint of enhancing the antibacterial characteristics of the antibacterial agent composition, the component (B1) is preferably gallic acid.

A content of the component (B1) in the antibacterial agent composition may be, for example, equal to or more than 0.001% by mass with respect to the total amount of the antibacterial agent composition from the viewpoint of enhancing the antibacterial characteristics, and the content is preferably equal to or more than 0.005% by mass, more preferably equal to or more than 0.01% by mass, even more preferably equal to or more than 0.1% by mass, and still more preferably equal to or more than 1% by mass.

From a similar point of view, the content of the component (B1) in the antibacterial agent composition may be, for example, equal to or less than 10% by mass with respect to the total amount of the antibacterial agent composition, and the content is preferably equal to or less than 5% by mass, more preferably equal to or less than 4% by mass, and even more preferably equal to or less than 3% by mass.

Furthermore, the content of the component (B1) with respect to the content of the component (A) ((B1)/(A)) in the antibacterial agent composition is, in a mass ratio, preferably equal to or more than 0.01, more preferably equal to or more than 0.015, and even more preferably equal to or more than 0.02, from the viewpoint of enhancing the antibacterial characteristics of the antibacterial agent composition.

From a similar point of view, the mass ratio ((B1)/(A)) is preferably equal to or less than 5, more preferably equal to or less than 1, even more preferably equal to or less than 0.5, and still more preferably equal to or less than 0.1.

The antibacterial agent composition may include components other than the above-mentioned components (A) and (B1).

According to the present embodiment, the antibacterial agent composition can be obtained by, for example, preparing the above-mentioned components (A) and (B1) and other components as appropriate, blending these at predetermined proportions, and mixing the components.

Furthermore, as another method for preparing the antibacterial agent composition, for example, a method of obtaining a culture liquid including a cyclic carboxylic acid by a bioprocess, and then obtaining a composition including the components (A) and (B1) through concentration purification of the culture liquid, may be mentioned. In the following description, a method for obtaining a culture liquid including the components (A) and (B1) by a bioprocess will be described.

In the bioprocess, the collection rate of the cyclic carboxylic acid and a derivative thereof can be enhanced by appropriately selecting the microorganism, the medium, the culturing facility, and the culture conditions.

The method for obtaining a culture liquid including the components (A) and (B1) by a bioprocess includes a raw material liquid preparation S01, an activated carbon treatment S02, a crystallization S03, and a solid-liquid separation S04.

(Raw Material Liquid Preparation S01)

First, a biomass is prepared. Here, the biomass refers to plant-derived organic resources. Specifically, the biomass includes products that have been converted into the forms of starch, cellulose, and the like and stored, animal bodies that grow by eating plants, and products that can be obtained by processing plant bodies and animal bodies.

More specifically, examples of the biomass include cellulose-based crops (pulp, kenaf, wheat straw, rice straw, waste paper, papermaking residue, and the like), wood, charcoal, compost, natural rubber, cotton, sugar cane, bean-curd dregs, fats and oils (rapeseed oil, cotton seed oil, soybean oil, coconut oil, castor oil, and the like), carbohydrate-based crops (corn, potatoes, wheat, rice, rice husks, rice bran, old rice, cassava, sago palm, and the like), bagasse, buckwheat, soybean, essential oils (wood turpentine oil, orange oil, eucalyptus oil, and the like), pulp black liquor, raw garbage, vegetable oil residue, aquatic product residue, livestock excrement, food waste, and wastewater sludge. More specifically, the biomass includes sugar cane strained lees.

—Pretreatment—

Next, the biomass is subjected to a pretreatment, and a mixed sugar is obtained.

Examples of such pretreatment include a physical treatment, a chemical treatment, a physicochemical treatment, and a biological treatment, and one kind or a combination of two or more kinds among these treatments is employed.

Among these, examples of the physical treatment include a miniaturization treatment by a disc mill, a grinder, or the like, a compression treatment, an electromagnetic wave irradiation treatment, and an electron beam irradiation treatment.

Examples of the chemical treatment include a treatment by an ionic liquid such as sulfuric acid, nitric acid, hydrochloric acid, phosphoric acid, or an alkali, a hydrothermal treatment, a subcritical water treatment, a supercritical fluid treatment, a treatment with a catalyst, an oxidizing agent treatment, a treatment of applying heat energy, and a treatment of applying light energy.

Examples of the physicochemical treatment include a steam blasting treatment and an ammonia blasting treatment.

Furthermore, examples of the biological treatment include treatments using fungi, bacteria, and the like.

In this manner, a mixed sugar is obtained. Examples of the obtainable mixed sugar include oligosaccharides or polysaccharides having glucose units. Specific examples include monosaccharides such as glucose, fructose, mannose, arabinose, xylose, and galactose; disaccharides such as cellobiose, sucrose, lactose, maltose, trehalose, cellobiose, and xylobiose; and polysaccharides such as dextrin and soluble starch.

Furthermore, as the mixed sugar, in addition to the above-described examples, saccharified liquids obtained by saccharifying straw (rice straw, barley straw, wheat straw, rye straw, oat straw, and the like); non-edible agricultural waste such as bagasse; energy crops such as switchgrass, napier grass, and miscanthus; wood chips, waste paper, and the like using diastatic enzymes, and, or those including molasses are also used.

—Preparation of Raw Material Liquid—

Next, a raw material liquid is prepared by culturing or reacting a microorganism or a transformant thereof in a reaction liquid containing a mixed sugar.

Microorganism or Transformant Thereof

It is preferable that a microorganism or a transformant thereof is cultured and grown in a medium prior to the reaction with the mixed sugar.

Culture Medium

As the medium to be used, a natural medium or a synthetic medium, both containing a carbon source, a nitrogen source, inorganic salts, other nutritive substances, and the like, may be mentioned. Specific examples of the medium include LB medium.

A concentration of the nitrogen source in the medium varies depending on the nitrogen source used; however, the concentration is adjusted to, for example, 0.1 to 10 (mass/v %).

A concentration of the inorganic salts in the medium varies depending on the inorganic salts used; however, the concentration is adjusted to, for example, 0.01 to 1 (mass/v %).

A concentration of the nutritive substances in the medium varies depending on the nutritive substances used; however, the concentration is adjusted to, for example, 0.1 to 10 (mass/v %).

Furthermore, vitamins can also be added, if necessary.

The pH of the medium is preferably 6 to 8.

Reaction Liquid

As the reaction liquid, a natural reaction liquid or a synthetic reaction liquid, both containing a carbon source, a nitrogen source, inorganic salts, and the like, is used.

Among these, the above-mentioned mixed sugar is used as the carbon source. A concentration of the mixed sugar in the reaction liquid is preferably 1 to 20 (mass/v %), more preferably 2 to 10 (mass/v %), and even more preferably 2 to 5 (mass/v %).

Furthermore, in addition to that, a carbon source suitably selected from the above-mentioned carbon sources is used. A concentration of all the carbon sources including the mixed sugar is preferably 2 to 5 (mass/v %).

As the nitrogen source, a nitrogen source suitably selected from the above-mentioned nitrogen sources is used. A concentration of the nitrogen source in the reaction liquid varies according to the concentration of the nitrogen source used; however, the concentration is adjusted to, for example, 0.01 to 1 (mass/v %).

As the inorganic salts, those suitably selected from the above-mentioned inorganic salts are used. A concentration of the nutritive substance in the reaction liquid varies according to the concentration of the nutritive substance used; however, the concentration is adjusted to, for example, 0.1 to 10 (mass/v %).

Furthermore, if necessary, vitamins suitably selected from the above-mentioned vitamins are used.

Reaction Conditions

The reaction temperature for the mixed sugar and the microorganism or a transformant thereof, that is, the survival temperature for the microorganism or a transformant thereof, is preferably 20° C. to 50° C., and more preferably 25° C. to 47° C., from the viewpoint of efficiently producing the cyclic carboxylic acid.

The reaction time is preferably 1 to 7 days, and more preferably 1 to 3 days.

The culture may be any of a batch type, a fed-batch type, or a continuous type; however, above all, batch type culture is preferable.

The reaction may be carried out under aerobic conditions or under reducing conditions.

Regarding a method for preparing the reaction liquid under reducing conditions, any known method can be used without limitation. For example, an aqueous solution for a reaction liquid under reducing conditions can be obtained by removing dissolved gas by a heat treatment or a depressurization treatment. In this case, dissolved gas (more specifically, dissolved oxygen) is removed by treating the culture liquid at a reduced pressure of preferably equal to or less than 10 mmHg, more preferably equal to or less than 5 mmHg, and even more preferably equal to or less than 3 mmHg, preferably for about 1 to 60 minutes, and more preferably about 5 to 40 minutes, and an aqueous solution for a reaction liquid under reducing conditions can be produced.

The aqueous solution for a reaction liquid under the reducing conditions may also be prepared by adding an appropriate reducing agent (for example, thioglycolic acid, ascorbic acid, cysteine hydrochloride, mercaptoacetic acid, thiol acetic acid, glutathione, or sodium sulfide).

Furthermore, these methods may be suitably combined.

When the reaction is carried out under reducing conditions, it is preferable that the reaction liquid is maintained under reducing conditions even during the reaction. In order to maintain the reducing conditions during the reaction, it is preferable to prevent contamination with oxygen from outside the reaction system as far as possible. Specifically, a method of enclosing the reaction system under an inert gas such as nitrogen gas or under carbon dioxide gas may be mentioned. As a method for more effectively preventing oxygen contamination, it may be necessary to suitably add an adjusting liquid to maintain the pH of the reaction system or solutions of various nutrients in order to efficiently bring out the intracellular metabolic functions of aerobic bacteria during the reaction; however, in such a case, it is preferable to have oxygen removed in advance from the solution to be added.

After a raw material liquid is prepared, the microorganism or a transformant thereof is separated and removed. Examples of the separation and removal method include a sedimentation separation method, a centrifugation method, and a filtration separation method. Furthermore, a method of combining a plurality of methods among these may also be used.

The present step may be provided as needed or may be replaced with preparing a liquid including a cyclic carboxylic acid produced by, for example, recycling.

—Concentration Treatment—

The obtained raw material liquid may be concentrated, if necessary.

Examples of the concentration method include distillation, adsorption, extraction, membrane separation, dialysis, and reverse osmosis, and one kind thereof or a combination of two or more kinds of these is used.

Among these, the concentration treatment is a treatment of bringing the raw material liquid into contact with a heated heat transfer surface and evaporating the solvent included in the raw material liquid, and it is preferably a treatment of bringing the raw material liquid repeatedly into contact with the heat transfer surface. According to such a treatment, when the solvent included in the raw material liquid is evaporated, since the heat transfer surface can be constantly wetted by the raw material liquid, the occurrence of charring can be suppressed.

Specifically, the raw material liquid is introduced into a stirring tank in which the inner wall surfaces are heat transfer surfaces, the raw material liquid collected at the bottom is pumped up, and the raw material liquid may be concentrated while using a device that stirs the raw material liquid while spraying it on the inner wall surface. As a result, the effective area of the heat transfer surface can be utilized maximally, and the concentration efficiency can be increased. Furthermore, the occurrence of charring due to drying of the heat transfer surface can be suppressed, and coloring of a precipitated solid can be suppressed.

The heating temperature in the concentration treatment is not limited; however, the heating temperature is preferably about 15° C. to 120° C., and more preferably about 20° C. to 90° C. As a result, the efficiency of concentration can be increased while suppressing the occurrence of charring and the denaturation of solutes.

Furthermore, the raw material solution for the concentration treatment may be placed under reduced pressure. As a result, volatilization of the solvent is accelerated, and the concentration efficiency can be increased. The pressure of the environment in which the raw material solution is placed is not limited; however, the pressure is preferably equal to or less than 80 kPa, and more preferably 0.1 to 50 kPa.

Upon the concentration, a salt of a cyclic carboxylic acid may be prepared using a basic substance and dissolved in an aqueous medium.

The concentration treatment may be performed as needed or may be omitted.

By concentrating the raw material liquid, the proportion (yield) of the amount of a solid that can be collected from a unit amount of the raw material liquid can be increased. Therefore, the time and energy required for the processes that will be described later can be reduced, and the production efficiency for the solid (solid production capacity per unit time) can be increased.

(Activated Carbon Treatment S02)

Next, the raw material liquid is subjected to an activated carbon treatment. Specifically, activated carbon is added to the raw material liquid, and the mixture is stirred. As a result, the solute of the raw material liquid can be decolorized.

Examples of the activated carbon include, but are not limited to, powdered activated carbon, granular activated carbon, fibrous activated carbon, sheet-shaped activated carbon, and honeycomb-shaped activated carbon.

The temperature for the activated carbon treatment is preferably about 10° C. to 150° C. The time for the activated carbon treatment is not limited; however, the time is preferably about 10 minutes to 40 hours.

The amount of the activated carbon to be added to 100 g of the raw material liquid is not limited; however, from the viewpoint of enjoying a sufficient decolorizing action while suppressing the adsorption of a solute to the activated carbon, the amount is preferably 0.01 to 10 g, and more preferably 0.1 to 5 g.

The activated carbon treatment may be performed as needed or may be omitted. The sequence of the activated carbon treatment is not limited to the present embodiment and may come, for example, after an elution.

Furthermore, the activated carbon after the treatment is removed by solid-liquid separation such as filtration.

(Crystallization S03)

Next, the raw material liquid is subjected to a crystallization treatment, and the solute of the raw material liquid is precipitated as a solid. According to such a crystallization treatment, since a process of precipitating a solid by lowering the solubility of the solute in the solution is carried out, a high-purity solid substance can be collected by performing a subsequent solid-liquid separation. Therefore, a cyclic carboxylic acid useful as a raw material for daily necessities, cosmetics, pharmaceuticals, and foods can be easily produced.

The crystallization treatment may be carried out by any method, as long as it is a treatment for precipitating a solute as a solid from the raw material liquid.

Specifically, examples include a treatment of changing the temperature of the raw material liquid and performing crystallization by utilizing the temperature-dependency of the solubility; a treatment of volatilizing and removing the solvent from the raw material liquid by operations such as heating or depressurization and performing crystallization; a treatment of adding a solvent with low solute solubility and performing crystallization by utilizing the solvent type dependency of the solubility; and a treatment of changing the pH of the raw material solution and performing crystallization by utilizing the pH responsiveness of the solubility, and any one kind or a combination of a plurality of kinds of these treatments is used.

For example, when a treatment of performing crystallization by utilizing the pH responsiveness is used, the solubility in water of the cyclic carboxylic acid included in the solute is generally decreased at a low pH. Therefore, by lowering the pH to, for example, about 1 to 4 in the crystallization, the solubility is lowered, and the solute can be precipitated.

The temperature at this time is not limited; however, the temperature is, for example, preferably about 15° C. to 80° C., and more preferably about 20° C. to 60° C. This makes it possible to achieve a balance between the capacity and yield of the crystallization treatment.

The crystallization operation may be a batch operation or a continuous operation.

Any known stirring tank is used for the crystallization operation.

In order to promote crystallization, a seed crystal containing a solid component to be precipitated may be added, if necessary. As a result, the seed crystal becomes a nucleus to promote crystallization, which leads to an increase in the crystallization efficiency, and an attempt to increase the purity is facilitated.

(Solid-Liquid Separation S04)

Next, a solid cyclic carboxylic acid is collected from the raw material liquid.

Examples of solid-liquid separation include filtration separation, sedimentation separation, reduced pressure dehydration, and pressure dehydration; however, filtration separation is preferably used from the viewpoints of the ease of operation and the accuracy of separation. Specifically, a centrifugal filter can be used.

Furthermore, the solid-liquid separation operation may be a batch operation or a continuous operation.

Subsequently, a washing operation is carried out by suitably using a poor solvent, and then the resulting solid is suitably dried.

As described above, an antibacterial agent composition in a solid form or the like including the components (A) and (B1) can be collected.

Furthermore, the obtained antibacterial agent composition may be used to obtain an antibacterial agent composition-mixed liquid including a medium such as water or ethanol. At this time, the content of the medium in the mixed liquid can be, for example, the balance remaining after excluding the components other than the medium in the mixed liquid.

The concentration of the component (A) in the mixed liquid may be, for example, equal to or more than 0.01% by mass, preferably equal to or more than 0.05% by mass, more preferably equal to or more than 0.15% by mass, even more preferably equal to or more than 0.25% by mass, and still more preferably equal to or more than 0.4% by mass, and the concentration may be, for example, equal to or less than 10% by mass, preferably equal to or less than 5% by mass, more preferably equal to or less than 3% by mass, even more preferably equal to or less than 2% by mass, and still more preferably equal to or less than 1% by mass.

The nature of the antibacterial agent composition obtainable in the present embodiment is not limited, and the antibacterial agent composition can be, for example, a solid form such as a powder form or a granular form, or a liquid form.

Furthermore, the antibacterial agent composition obtainable in the present embodiment can be used for daily necessities, cosmetics, pharmaceuticals, foods, and the like, and above all, the antibacterial agent composition is suitably used for daily necessities and cosmetics.

Specific examples of the daily necessities include an antibacterial agent, an antifungal agent, a deodorant, a detergent, a sanitary article, a bathing article, a household chemical product, and an oral care article.

Furthermore, examples of the cosmetics include an emulsion, a cream, a foundation, an eye shadow, a lipstick, a cheek blusher, a hair cosmetic, an emollient cream, an emollient lotion, a cream conditioner, a cold cream, a burnishing cream, a lotion, a facial mask, a gel, a face pack, a soap, a body soap, a shampoo, a hair conditioner, a rinsing conditioner, a bath additive, a body wash, a face wash, a shaving cream, a hair cream, a hair lotion, a hair treatment, a hair pack, a lip gloss, and a lip cream.

The antibacterial agent composition according to the present embodiment can be suitably used for suppressing the growth of one kind or two or more kinds selected from the group consisting of *Staphylococcus aureus, Escherichia coli,* and *Pseudomonas aeruginosa,* which are bacteria; *Candida,* which is yeast; and *Aspergillus niger,* which is a fungus.

The present embodiment includes the following aspects.

I-1. An antibacterial agent composition including the following components (A) and (B1):
(A) a cyclic carboxylic acid (excluding the following component (B1)), and
(B1) one or more selected from the group consisting of gallic acid and an ester thereof;

I-2. The antibacterial agent composition according to I-1., in which the component (A) is one or more selected from the group consisting of protocatechuic acid, shikimic acid, 4-hydroxybenzoic acid, 4-aminobenzoic acid, and ferulic acid.

I-3. The antibacterial agent composition according to I-1. or I-2., in which a content of the component (B1) with respect to the content of the component (A) ((B1)/(A)) in the antibacterial agent composition is equal to or more than 0.01 and equal to or less than 5 in a mass ratio.

Second Embodiment

The present embodiment relates to a water-soluble additive composition.

As a technology for enhancing the solubility of a cyclic carboxylic acid, there is the technology described in Patent Document 5 (Japanese Unexamined Patent Publication No. 2018-150288). In the same patent document, as a technology for providing crystals of a protocatechuic acid (PCA) cationic salt which has excellent solubility and is stable under high humidity conditions, and a method for producing the crystals, there is described a method for producing crystals of a PCA cationic salt, the method including: dropping or adding an alcohol solution or a nitrile solution to an alcohol solution of PCA in which a cation-containing compound is dissolved, to precipitate crystals of a PCA cationic salt; and collecting the crystals of the PCA cationic salt from the solution.

The present inventors examined the technology described in the above-mentioned Patent Document 5, and it was found that there is still room for improvement in view of obtaining a composition in which the purity of the cyclic carboxylic acid is high and the cyclic carboxylic acid has excellent water-solubility.

According to the present embodiment,
there is provided a water-soluble additive composition including a cyclic carboxylic acid,
in which the total content of $Na^+$ and $NH_4^+$ is equal to or more than 100 ppm and equal to or less than 5000 ppm with respect to the cyclic carboxylic acid.

Furthermore, according to the present embodiment,
there is provided a water-soluble additive composition including a cyclic carboxylic acid,
in which the total inorganic ion content (excluding hydrogen ions and hydroxyl group ions) is equal to or more than 300 ppm and equal to or less than 5000 ppm with respect to the cyclic carboxylic acid.

Furthermore, according to the present embodiment, for example, daily necessities or cosmetics having the water-soluble additive composition according to the above-mentioned embodiment incorporated therein can be obtained.

According to the present embodiment, a composition in which the purity of the cyclic carboxylic acid is high and the cyclic carboxylic acid has excellent water solubility, can be provided.

Hereinafter, embodiments will be described more specifically. According to the present embodiment, the composition can include each of the components singly or in combination of two or more kinds thereof.

Embodiment 2-1

According to the present embodiment, the water-soluble additive composition includes a cyclic carboxylic acid. The total content of $Na^+$ and $NH_4^+$ in the water-soluble additive composition is equal to or more than 100 ppm and equal to or less than 5000 ppm with respect to the cyclic carboxylic acid.

Embodiment 2-2

According to the present embodiment, the water-soluble additive composition includes a cyclic carboxylic acid. The total inorganic ion content (excluding hydrogen ions and hydroxyl group ions) in the water-soluble additive composition is equal to or more than 300 ppm and equal to or less than 5000 ppm with respect to the cyclic carboxylic acid.

Hereinafter, the constituent components of the water-soluble additive composition will be described more specifically. The following configurations can be used for each of the above-mentioned embodiments. Furthermore, the configuration described in each of the above-described embodiments can be used in combination with other embodiments.

(Cyclic Carboxylic Acid)

Specific examples of the cyclic carboxylic acid include a cyclic carboxylic acid having one or two or more hydroxy groups; and a cyclic carboxylic acid having one or two or more amino groups.

Examples of the cyclic carboxylic acid having a hydroxy group include an aromatic hydroxycarboxylic acid and an alicyclic hydroxycarboxylic acid.

Examples of the aromatic hydroxycarboxylic acid include hydroxybenzoic acids such as salicylic acid and 4-hydroxybenzoic acid, monohydroxybenzoic acids such as hydroxy(methyl)benzoic acid and hydroxy(methoxy)benzoic acid, and derivatives thereof;

dihydroxybenzoic acids, such as dihydroxybenzoic acids such as protocatechuic acid and gentisic acid, dihydroxy(methyl)benzoic acids such as orsellinic acid, and derivatives thereof; and monohydroxycinnamic acids such as ferulic acid, and derivatives thereof.

Examples of the alicyclic hydroxycarboxylic acid include shikimic acid and quinic acid.

Furthermore, examples of the cyclic carboxylic acid having an amino group include monoaminobenzoic acids such as 4-aminobenzoic acid, derivatives thereof, and other aromatic aminocarboxylic acids; and alicyclic aminocarboxylic acids.

From the viewpoint of stably enhancing the water solubility of the water-soluble additive composition, the cyclic carboxylic acid is preferably one or more selected from the group consisting of protocatechuic acid, shikimic acid, 4-hydroxybenzoic acid, 4-aminobenzoic acid, and ferulic acid, and more preferably one or more selected from the group consisting of protocatechuic acid and shikimic acid.

The content of the cyclic carboxylic acid in the water-soluble additive composition is preferably equal to or more than 95% by mass, more preferably equal to or more than 95.3% by mass, and even more preferably equal to or more than 95.6% by mass, with respect to the total amount of the water-soluble additive composition from the viewpoint of obtaining a composition with a higher concentration.

Furthermore, from the viewpoint of enhancing the water solubility of the water-soluble additive composition, the content of the cyclic carboxylic acid in the water-soluble additive composition is less than 100% by mass with respect to the total amount of the water-soluble additive composition, and for example, the content may be equal to or less than 99.97% by mass, preferably equal to or less than 99.9% by mass, more preferably equal to or less than 99.5% by mass, and even more preferably equal to or less than 99% by mass.

The total content of $Na^+$ and $NH_4^+$ in the water-soluble additive composition is preferably equal to or more than 100 ppm, more preferably equal to or more than 200 ppm, and even more preferably equal to or more than 300 ppm, with respect to the cyclic carboxylic acid from the viewpoint of stably enhancing the water solubility of the cyclic carboxylic acid in the water-soluble additive composition.

From a similar point of view, the total content of $Na^+$ and $NH_4^+$ in the water-soluble additive composition is preferably equal to or less than 5000 ppm, more preferably equal to or less than 2000 ppm, even more preferably equal to or less than 1000 ppm, and still more preferably equal to or less than 500 ppm, with respect to the cyclic carboxylic acid.

The content of $Na^+$ in the water-soluble additive composition may be, for example, equal to or more than 10 ppm or, for example, equal to or more than 90 ppm with respect to the cyclic carboxylic acid from the viewpoint of stably enhancing the water solubility of the cyclic carboxylic acid in the water-soluble additive composition, and the content is preferably equal to or more than 100 ppm, more preferably equal to or more than 200 ppm, and even more preferably equal to or more than 300 ppm.

From a similar point of view, the content of $Na^+$ in the water-soluble additive composition is preferably equal to or less than 5000 ppm, more preferably equal to or less than 4500 ppm, even more preferably equal to or less than 4000 ppm, still more preferably equal to or less than 3000 ppm, even more preferably equal to or less than 1000 ppm, and still more preferably equal to or less than 500 ppm, with respect to the cyclic carboxylic acid.

The content of $NH_4^+$ in the water-soluble additive composition may be, for example, equal to or more than 10 ppm with respect to the cyclic carboxylic acid from the viewpoint of stably enhancing the water solubility of the cyclic carboxylic acid in the water-soluble additive composition, and the content is preferably equal to or more than 100 ppm, more preferably equal to or more than 200 ppm, and even more preferably equal to or more than 300 ppm.

From a similar point of view, the content of $NH_4^+$ in the water-soluble additive composition is preferably equal to or less than 5000 ppm, more preferably equal to or less than 2000 ppm, even more preferably equal to or less than 1000 ppm, and still more preferably equal to or less than 500 ppm, with respect to the cyclic carboxylic acid.

Here, the contents of $Na^+$ and $NH_4^+$ in the water-soluble additive composition and the contents of $K^+$, $SO_4^{2-}$, $PO_4^{3-}$, $NO_2^-$, $NO_3^-$, and $Cl^-$, which will be described later, are all measured by ion chromatography or capillary electrophoresis.

The total inorganic ion content (excluding hydrogen ions and hydroxyl group ions) in the water-soluble additive composition is preferably equal to or more than 300 ppm, more preferably equal to or more than 500 ppm, even more preferably equal to or more than 800 ppm, and still more preferably equal to or more than 1500 ppm, with respect to the cyclic carboxylic acid from the viewpoint of stably enhancing the water solubility of the cyclic carboxylic acid in the water-soluble additive composition.

From a similar point of view, the total inorganic ion content (excluding hydrogen ions and hydroxyl group ions) in the water-soluble additive composition is preferably equal to or less than 5000 ppm, more preferably equal to or less than 4000 ppm, even more preferably equal to or less than 3000 ppm, and still more preferably equal to or less than 2000 ppm, with respect to the cyclic carboxylic acid.

Here, among the inorganic ions (excluding hydrogen ions and hydroxyl group ions) included in the water-soluble additive composition, examples of inorganic ions other than the above-mentioned $Na^+$ and $NH_4^+$ include cations such as $K^+$; and anions such as $SO_4^{2-}$, $PO_4^{3-}$, $NO_2^-$, $NO_3^-$, and $Cl^-$.

The content of $K^+$ in the water-soluble additive composition is equal to or more than 0 ppm with respect to the cyclic carboxylic acid.

When the water-soluble additive composition includes $K^+$, the content thereof may be, for example, equal to or more than 10 ppm, and preferably equal to or more than 50 ppm, with respect to the cyclic carboxylic acid from the viewpoint of stably enhancing the water solubility of the cyclic carboxylic acid in the water-soluble additive composition.

From a similar point of view, the content of $K^+$ in the water-soluble additive composition is preferably equal to or less than 200 ppm, and more preferably equal to or less than 100 ppm, with respect to the cyclic carboxylic acid.

The content of $SO_4^{2-}$ in the water-soluble additive composition is equal to or more than 0 ppm with respect to the cyclic carboxylic acid.

When the water-soluble additive composition includes $SO_4^{2-}$, the content thereof is preferably equal to or less than 1000 ppm, more preferably equal to or less than 500 ppm, and even more preferably equal to or less than 100 ppm, with respect to the cyclic carboxylic acid.

Furthermore, the content of $SO_4^{2-}$ may be, for example, equal to or more than 10 ppm with respect to the cyclic carboxylic acid.

The content of $PO_4^{3-}$ in the water-soluble additive composition is equal to or more than 0 ppm and may be, for example, equal to or more than 10 ppm, with respect to the cyclic carboxylic acid.

When the water-soluble additive composition includes $PO_4^{3-}$, the content thereof is preferably equal to or less than 500 ppm, more preferably equal to or less than 300 ppm, and even more preferably equal to or less than 200 ppm, with respect to the cyclic carboxylic acid.

The content of $NO_2^-$ in the water-soluble additive composition is equal to or more than 0 ppm and may be, for example, equal to or more than 1 ppm, with respect to the cyclic carboxylic acid.

When the water-soluble additive composition includes $NO_2^-$, the content thereof is preferably equal to or less than 100 ppm, more preferably equal to or less than 50 ppm, and even more preferably equal to or less than 30 ppm, with respect to the cyclic carboxylic acid.

The content of $NO_3^-$ in the water-soluble additive composition is equal to or more than 0 ppm and may be, for example, equal to or more than 10 ppm, with respect to the cyclic carboxylic acid.

When the water-soluble additive composition includes $NO_3^-$, the content thereof is preferably equal to or less than 100 ppm, more preferably equal to or less than 50 ppm, and even more preferably equal to or less than 30 ppm, with respect to the cyclic carboxylic acid.

The content of $Cl^-$ in the water-soluble additive composition is equal to or more than 0 ppm and may be, for example, equal to or more than 5 ppm, with respect to the cyclic carboxylic acid.

When the water-soluble additive composition includes $Cl^-$, the content thereof is preferably equal to or less than 100 ppm, more preferably equal to or less than 50 ppm, and even more preferably equal to or less than 30 ppm, with respect to the cyclic carboxylic acid.

The water-soluble additive composition may include components other than the above-mentioned cyclic carboxylic acid.

For example, the water-soluble additive composition may also include a medium such as water or ethanol. At this time, the content of the medium in the composition can be, for example, the balance remaining after excluding the components other than the medium in the composition.

Next, a method for producing a water-soluble additive composition will be described.

As a method for preparing a water-soluble additive composition, for example, a method of obtaining a culture liquid including a cyclic carboxylic acid by a bioprocess through a method that will be described later and then obtaining a composition including the cyclic carboxylic acid by concentration purification of the culture liquid, may be mentioned.

Here, in order to control the total content of $Na^+$ and $NH^{4+}$ or the total inorganic ion content to be within the above-mentioned specific range, it is important to appropriately select the conditions for producing the cyclic carboxylic acid in the bioprocess as well as to appropriately select the purification conditions. For example, as the purification conditions, the conditions for concentration and filtration and the number of times of washing are appropriately selected.

With regard to the water-soluble additive composition obtainable in the present embodiment, since the total content of $Na^+$ and $NH_4^+$ or the total inorganic ion content is in a specific range, the purity of the cyclic carboxylic acid is high, and the cyclic carboxylic acid has excellent water-solubility.

In the following description, a method for obtaining a culture liquid including a cyclic carboxylic acid by a bioprocess will be described.

The method for obtaining a culture liquid including a cyclic carboxylic acid by a bioprocess includes a raw material liquid preparation S01, an activated carbon treatment S02, a crystallization S03, and a solid-liquid separation S04.

(Raw Material Liquid Preparation S01)

The raw material liquid preparation S01 can be carried out according to, for example, the raw material liquid preparation S01 described in the first embodiment. For example, regarding the materials, procedure, method, conditions, and the like used in the raw material liquid preparation S01, for example, those described in the first embodiment can be used.

(Activated Carbon Treatment S02)

The activated carbon treatment S02 can be suitably carried out according to, for example, the activated carbon treatment S02 described in the first embodiment. For example, regarding the materials, procedure, method, conditions and the like used in the activated carbon treatment S02, for example, those described in the first embodiment can be used.

(Crystallization S03)

The crystallization S03 can be carried out, for example, according to the crystallization S03 described in the first embodiment. For example, regarding the materials, procedure, method, conditions and the like used in the crystallization S03, for example, those described in the first embodiment can be used.

(Solid-Liquid Separation S04)

The solid-liquid separation S04 can be carried out according to, for example, the solid-liquid separation S04 described in the first embodiment. For example, regarding the materials, procedure, method, conditions, and the like used in the solid-liquid separation S04, for example, those described in the first embodiment can be used.

Subsequently, a washing operation is carried out by suitably using a poor solvent, and then the resulting solid is suitably dried.

As described above, for example, by appropriately selecting the purification conditions, a water-soluble additive composition in a solid form or the like, in which the ion content is in a specific range, can be collected.

The nature of the water-soluble additive composition obtainable in the present embodiment is not limited, and the water-soluble additive composition can be, for example, a solid form such as a powder form or a granular form, or a liquid form.

Furthermore, the water-soluble additive composition obtainable in the present embodiment can be used for daily necessities, cosmetics, pharmaceuticals, foods, and the like, and above all, the water-soluble additive composition is suitably used for daily necessities and cosmetics.

Examples of the daily necessities include an antibacterial agent, an antifungal agent, a deodorant, a detergent, a sanitary article, a bathing article, a household chemical product, and an oral care article.

Furthermore, examples of the cosmetics include an emulsion, a cream, a foundation, an eye shadow, a lipstick, a cheek blusher, a hair cosmetic, an emollient cream, an emollient lotion, a cream conditioner, a cold cream, a burnishing cream, a lotion, a facial mask, a gel, a face pack, a soap, a body soap, a shampoo, a hair conditioner, a rinsing conditioner, a bath additive, a body wash, a face wash, a shaving cream, a hair cream, a hair lotion, a hair treatment, a hair pack, a lip gloss, a lip cream, and the like.

Furthermore, according to the present embodiment, the water-soluble additive composition can be used as, for example, an antibacterial agent or a taste potentiator.

The present embodiment includes the following aspects.

II-1. A water-soluble additive composition including a cyclic carboxylic acid,
in which the total content of $Na^+$ and $NH_4^+$ is equal to or more than 100 ppm and equal to or less than 5000 ppm with respect to the cyclic carboxylic acid.

II-2. A water-soluble additive composition including a cyclic carboxylic acid,
in which the total inorganic ion content (excluding hydrogen ions and hydroxyl group ions) is equal to or more than 300 ppm and equal to or less than 5000 ppm with respect to the cyclic carboxylic acid.

II-3. The water-soluble additive composition according to II-1. or II-2., in which the cyclic carboxylic acid is one or more selected from the group consisting of protocatechuic acid, shikimic acid, 4-hydroxybenzoic acid, 4-aminobenzoic acid, and ferulic acid.

II-4. The water-soluble additive composition according to any one of II-1. to II-3., in which a content of the cyclic carboxylic acid in the water-soluble additive composition is equal to or more than 95% by mass and equal to or less than 99.9% by mass with respect to the total amount of the water-soluble additive composition.

Third Embodiment

The present embodiment relates to a water-soluble additive composition.

As technologies related to a composition having a cyclic carboxylic acid incorporated therein, those described in Patent Document 6 (Japanese Unexamined Patent Publication No. 2014-31347) and Patent Document 7 (WO 2016/039407), which are described in the section of Background Art, may be mentioned.

The present inventors examined the technologies described in the above-described Patent Documents 6 and 7, and it was found that there is room for improvement in terms of enhancing the moisture-retaining property and the antibacterial characteristics.

Thus, the present embodiment provides a composition having excellent moisture-retaining property and antibacterial characteristics.

According to the present embodiment,
there is provided a water-soluble additive composition including the following components (A) and (B2):
(A) a cyclic carboxylic acid (excluding the following component (B2)), and
(B2) an amino acid.

Furthermore, according to the present embodiment, for example, daily necessities or cosmetics having the water-soluble additive composition according to the above-mentioned embodiment incorporated therein can be obtained.

According to the present embodiment, a composition having excellent moisture-retaining property and antibacterial characteristics can be provided.

Hereinafter, embodiments will be described more specifically. According to the present embodiment, the composition can include each of the components singly or in combination of two or more kinds thereof.

According to the present embodiment, the water-soluble additive composition includes the following components (A) and (B2):
(A) a cyclic carboxylic acid (excluding the following component (B2)), and
(B2) an amino acid.

(Component (A))

Component (A) is a cyclic carboxylic acid and is a component other than component (B2) that will be described later.

Specific examples of the component (A) include a cyclic carboxylic acid having one or two or more hydroxy groups; and a cyclic carboxylic acid having one or two or more amino groups.

Examples of the cyclic carboxylic acid having a hydroxy group include an aromatic hydroxycarboxylic acid and an alicyclic hydroxycarboxylic acid.

Examples of the aromatic hydroxycarboxylic acid include hydroxybenzoic acids such as salicylic acid and 4-hydroxybenzoic acid, monohydroxybenzoic acids such as hydroxy(methyl)benzoic acid and hydroxy(methoxy)benzoic acid, and derivatives thereof;

dihydroxybenzoic acids, such as dihydroxybenzoic acids such as protocatechuic acid and gentisic acid, dihydroxy(methyl)benzoic acids such as orsellinic acid, and derivatives thereof; and monohydroxycinnamic acids such as ferulic acid, and derivatives thereof.

Examples of the alicyclic hydroxycarboxylic acid include shikimic acid and quinic acid.

Furthermore, examples of the cyclic carboxylic acid having an amino group include monoaminobenzoic acids such as 4-aminobenzoic acid, derivatives thereof, and other aromatic aminocarboxylic acids; and alicyclic aminocarboxylic acids.

From the viewpoint of enhancing the moisture-retaining property and antibacterial characteristics of the water-soluble additive composition, the component (A) is preferably one or more selected from the group consisting of protocatechuic acid, shikimic acid, 4-hydroxybenzoic acid, 4-aminobenzoic acid, and ferulic acid; and more preferably one or more selected from the group consisting of protocatechuic acid and shikimic acid.

The content of the component (A) in the water-soluble additive composition is preferably equal to or more than 95% by mass, more preferably equal to or more than 97% by mass, and even more preferably equal to or more than 98% by mass, with respect to the total amount of the water-soluble additive composition, from the viewpoint of enhancing the moisture-retaining property and the antibacterial characteristics.

From a similar point of view, the content of the component (A) in the water-soluble additive composition is less than 100% by mass with respect to the total amount of the water-soluble additive composition, and the content may be, for example, equal to or less than 99.999% by mass, or for example, equal to or less than 99.98% by mass and is preferably equal to or less than 99.9% by mass, more preferably equal to or less than 99.5% by mass, and even more preferably equal to or less than 99% by mass.

(Component (B2))

Component (B2) is an amino acid. Examples of the component (B2) include neutral amino acids, acidic amino acids, and basic amino acids.

Examples of the neutral amino acids include aliphatic amino acids such as glycine, alanine, valine, leucine, and isoleucine;

oxyamino acids such as serine and threonine;

sulfur-containing amino acids such as cysteine, cystine, and methionine;

aromatic amino acids such as phenylalanine, tyrosine, and tryptophan;

imino acids such as proline; and acetate amino acid amides such as asparagine and glutamine.

Examples of the acidic amino acids include aspartic acid and glutamic acid.

Examples of the basic amino acids include lysine, histidine, and arginine.

From the viewpoint of enhancing the moisture-retaining property and antibacterial characteristics of the water-soluble additive composition, the component (B2) is preferably one or two or more amino acids selected from the group consisting of glutamic acid, alanine, valine, glycine, aspartic acid, serine, histidine, threonine, arginine, tyrosine, cystine, methionine, phenylalanine, isoleucine, leucine, lysine, and proline; more preferably one or two or more amino acids selected from the group consisting of aspartic acid, glutamic acid, glycine, alanine, valine, isoleucine, lysine, and proline; and even more preferably glutamic acid.

The content of the component (B2) in the water-soluble additive composition may be, for example, equal to or more than 0.001% by mass with respect to the total amount of the water-soluble additive composition from the viewpoint of enhancing the moisture-retaining property and antibacterial characteristics, and the content is preferably equal to or more than 0.005% by mass, more preferably equal to or more than 0.01% by mass, even more preferably equal to or more than 0.1% by mass, and still more preferably equal to or more than 1% by mass.

From a similar point of view, the content of the component (B2) in the water-soluble additive composition may be, for example, equal to or less than 5% by mass with respect to the total amount of the water-soluble additive composition, and the content is preferably equal to or less than 4% by mass, more preferably equal to or less than 3% by mass, and even more preferably equal to or less than 2% by mass.

The water-soluble additive composition preferably includes glutamic acid, and the content of glutamic acid in the water-soluble additive composition is preferably equal to or more than 0.001% by mass, more preferably equal to or more than 0.01% by mass, and even more preferably equal to or more than 0.1% by mass, with respect to the total amount of the water-soluble additive composition from the viewpoint of enhancing the moisture-retaining property and antibacterial characteristics of the water-soluble additive composition.

From a similar point of view, when the water-soluble additive composition includes glutamic acid, the content of glutamic acid in the water-soluble additive composition is preferably equal to or less than 5% by mass, more preferably equal to or less than 1% by mass, even more preferably equal to or less than 0.5% by mass, and still more preferably equal to or less than 0.2% by mass, with respect to the entire water-soluble additive composition.

When the water-soluble additive composition includes aspartic acid, the content of aspartic acid in the water-soluble additive composition is preferably equal to or more than 1 ppm, and more preferably equal to or more than 10 ppm and is preferably equal to or less than 200 ppm, and more preferably equal to or less than 50 ppm, with respect to the total amount of the water-soluble additive composition from the viewpoint of enhancing the moisture-retaining property and the antibacterial characteristics of the water-soluble additive composition.

When the water-soluble additive composition includes glycine, the content of glycine in the water-soluble additive composition is preferably equal to or more than 1 ppm, and more preferably equal to or more than 10 ppm and is preferably equal to or less than 200 ppm, and more preferably equal to or less than 100 ppm, with respect to the total amount of the water-soluble additive composition from the viewpoint of enhancing the moisture-retaining property and the antibacterial characteristics of the water-soluble additive composition.

When the water-soluble additive composition includes alanine, the content of alanine in the water-soluble additive composition is preferably equal to or more than 10 ppm, and more preferably equal to or more than 50 ppm and is preferably equal to or less than 3000 ppm, and more preferably equal to or less than 1000 ppm, with respect to the total amount of the water-soluble additive composition from the viewpoint of enhancing the moisture-retaining property and the antibacterial characteristics of the water-soluble additive composition.

When the water-soluble additive composition includes valine, the content of valine in the water-soluble additive composition is preferably equal to or more than 1 ppm, and more preferably equal to or more than 10 ppm and is preferably equal to or less than 500 ppm, and more preferably equal to or less than 200 ppm, with respect to the total amount of the water-soluble additive composition from the viewpoint of enhancing the moisture-retaining property and the antibacterial characteristics of the water-soluble additive composition.

When the water-soluble additive composition includes isoleucine, the content of isoleucine in the water-soluble additive composition is preferably equal to or more than 1 ppm, and more preferably equal to or more than 2 ppm and is preferably equal to or less than 20 ppm, and more preferably equal to or less than 10 ppm, with respect to the total amount of the water-soluble additive composition from the viewpoint of enhancing the moisture-retaining property and the antibacterial characteristics of the water-soluble additive composition.

When the water-soluble additive composition includes proline, the content of proline in the water-soluble additive composition is preferably equal to or more than 5 ppm, and more preferably equal to or more than 50 ppm and is preferably equal to or less than 1000 ppm, and more preferably equal to or less than 500 ppm, with respect to the total amount of the water-soluble additive composition from the viewpoint of enhancing the moisture-retaining property and the antibacterial characteristics of the water-soluble additive composition.

The water-soluble additive composition may include components other than the above-mentioned components (A) and (B2).

For example, the water-soluble additive composition may also include a medium such as water or ethanol. At this time, the content of the medium in the composition can be, for example, the balance remaining after excluding the components other than the medium in the composition.

Next, a method for producing a water-soluble additive composition will be described.

According to the present embodiment, the water-soluble additive composition can be obtained by, for example, preparing the above-mentioned components (A) and (B2) and other components as appropriate, blending these at predetermined proportions, and mixing them.

Furthermore, as another method for preparing the water-soluble additive composition, for example, a method of obtaining a culture liquid including the components (A) and (B2) by a bioprocess, and then obtaining a composition including the components (A) and (B2) through concentration purification of the culture liquid, may be mentioned. In the following description, a method for obtaining a culture liquid including a cyclic carboxylic acid by a bioprocess will be described.

The method for obtaining a culture liquid including the components (A) and (B2) by a bioprocess includes a raw material liquid preparation S01, an activated carbon treatment S02, a crystallization S03, and a solid-liquid separation S04.

(Raw Material Liquid Preparation S01)

The raw material liquid preparation S01 can be carried out according to, for example, the raw material liquid preparation S01 described in the first embodiment. For example, regarding the materials, procedure, method, conditions, and the like used in the raw material liquid preparation S01, for example, those described in the first embodiment can be used.

(Activated Carbon Treatment S02)

The activated carbon treatment S02 can be suitably carried out according to, for example, the activated carbon treatment S02 described in the first embodiment. For example, regarding the materials, procedure, method, conditions and the like used in the activated carbon treatment S02, for example, those described in the first embodiment can be used.

(Crystallization S03)

The crystallization S03 can be carried out, for example, according to the crystallization S03 described in the first embodiment. For example, regarding the materials, procedure, method, conditions and the like used in the crystallization S03, for example, those described in the first embodiment can be used.

(Solid-Liquid Separation S04)

The solid-liquid separation S04 can be carried out according to, for example, the solid-liquid separation S04 described in the first embodiment. For example, regarding the materials, procedure, method, conditions, and the like used in the solid-liquid separation S04, for example, those described in the first embodiment can be used.

Subsequently, a washing operation is carried out by suitably using a poor solvent, and then the resulting solid is suitably dried.

As described above, a water-soluble additive composition in a solid form or the like including the components (A) and (B2) can be collected.

The nature of the water-soluble additive composition obtainable in the present embodiment is not limited, and the water-soluble additive composition can be, for example, a solid form such as a powder form or a granular form, or a liquid form.

Furthermore, the water-soluble additive composition obtainable in the present embodiment can be used for daily necessities, cosmetics, pharmaceuticals, foods, and the like, and above all, the water-soluble additive composition is suitably used for daily necessities and cosmetics.

Specific examples of the daily necessities include an antibacterial agent, an antifungal agent, a deodorant, a detergent, a sanitary article, a bathing article, a household chemical product, and an oral care article.

Furthermore, examples of the cosmetics include an emulsion, a cream, a foundation, an eye shadow, a lipstick, a cheek blusher, a hair cosmetic, an emollient cream, an emollient lotion, a cream conditioner, a cold cream, a burnishing cream, a lotion, a facial mask, a gel, a face pack, a soap, a body soap, a shampoo, a hair conditioner, a rinsing conditioner, a bath additive, a body wash, a face wash, a shaving cream, a hair cream, a hair lotion, a hair treatment, a hair pack, a lip gloss, and a lip cream.

Furthermore, according to the present embodiment, the water-soluble additive composition can be used as, for example, a moisturizing agent or an antibacterial agent.

Furthermore, according to the present embodiment, for example, it is also possible to obtain a water-soluble additive composition having low irritation to the skin.

The present embodiment includes the following aspects.

III-1. A water-soluble additive composition including the following components (A) and (B2):
 (A) a cyclic carboxylic acid (excluding the following component (B2)), and
 (B) an amino acid.

III-2. The water-soluble additive composition according to in which the component (A) is one kind or two or more kinds selected from the group consisting of protocatechuic acid, shikimic acid, 4-hydroxybenzoic acid, 4-aminobenzoic acid, and ferulic acid.

III-3. The water-soluble additive composition according to III-1. or III-2., in which the component (B2) includes one or two or more amino acids selected from the group consisting of glutamic acid, alanine, valine, glycine, aspartic acid, serine, histidine, threonine, arginine, tyrosine, cystine, methionine, phenylalanine, isoleucine, leucine, lysine, and proline.

III-4. The water-soluble additive composition according to any one of III-1. to III-3., in which the content of the component (A) in the water-soluble additive composition is equal to or more than 95% by mass and equal to or less than 99.9% by mass.

III-5. The water-soluble additive composition according to any one of III-1. to III-4., in which the content of the component (B2) in the water-soluble additive composition is equal to or more than 0.001% by mass and equal to or less than 5% by mass.

III-6. The water-soluble additive composition according to any one of III-1. to III-5., in which the component (B2) includes glutamic acid, and the content of the glutamic acid in the water-soluble additive composition is equal to or more than 0.001% by mass and equal to or less than 1% by mass.

Fourth Embodiment

The present embodiment relates to a food, a food additive, and a method for producing a cyclic compound or a derivative thereof.

Cyclic compounds having a specific structure are known to be used as food additives. For example, it is described in Patent Document 8 (Japanese Unexamined Patent Publication No. 2007-238469) that aromatic hydroxycarboxylic acids are important as antiseptics and preservatives for foods.

However, cyclic compounds such as those described above are usually obtained from petroleum. In such a case, a petroleum-derived cyclic compound (chemical product)

that can be collected by fractional distillation refining of petroleum is a so-called basic compound having a simple chemical structure. On the other hand, a high value-added compound having a more complicated chemical structure has to be derived from this basic compound through a synthesis process. In this case, unless petroleum is fractionated and refined at a high level while disregarding the production cost, various isomers derived from raw materials and synthesis processes, trace components derived from catalysts, ionic components, mineral components, and the like may remain in the petroleum-derived chemical products. It cannot be said that these impurities included in the petroleum-derived chemical products are preferable from the viewpoint of safety to the human body.

An object of the present embodiment is to provide a safer food and a safer food additive, both of which do not include petroleum-derived impurities. Another object of the present invention is to provide a method for producing a cyclic compound or a derivative thereof, both of which can be used as a food or a food additive.

Such an object is achieved by the present embodiment described in the following (VI-1) to (VI-10).

(VI-1) A food containing at least one of a cyclic compound derived from a plant-derived saccharide and a microorganism and a derivative of the cyclic compound.

(VI-2) The food according to the above-described item (VI-1), in which the cyclic compound is a compound represented by the following General Formula (1):

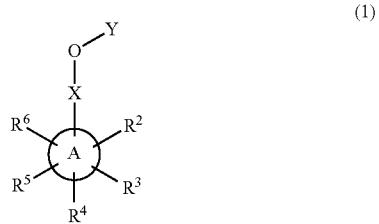

(1)

wherein in the General Formula (1), a ring A represents a 5-membered ring of a saturated ring, a partially saturated ring, or an aromatic ring, or a 6-membered ring of a saturated ring, a partially saturated ring, or an aromatic ring; X represents a single bond or a bond including one or more carbons; Y represents a hydrogen atom or an alkyl group; and $R^2$ to $R^6$ (in a case where the ring A is a 5-membered ring, $R^2$ to $R^5$) each independently represent a hydrogen atom, a hydroxyl group, an amino group, an alkoxy group, a carboxyl group, or a carbonyl group.

(VI-3) The food according to the above-described item (VI-2), in which the cyclic compound is at least one selected from the group consisting of 2-hydroxybenzoic acid, 3-hydroxybenzoic acid, 4-hydroxybenzoic acid, 2,3-dihydroxybenzoic acid, 2,4-dihydroxybenzoic acid, 2,5-dihydroxybenzoic acid, 2,6-dihydroxybenzoic acid, 3,4-dihydroxybenzoic acid, and 3,5-dihydroxybenzoic acid.

(VI-4) The food according to the above-described item (VI-2), in which when ring A of the cyclic compound is a 5-membered ring of a saturated ring or a partially saturated ring, in which all the ring-constituting atoms are carbon atoms, one or more of the carbon atoms of ring A to which $R^2$ to $R^5$ and X are bonded are asymmetric carbon atoms, and when ring A of the cyclic compound is a 6-membered ring of a saturated ring or a partially saturated ring, in which all the ring-constituting atoms are carbon atoms, one or more of the carbon atoms of ring A to which $R^2$ to $R^6$ and X are bonded are asymmetric carbon atoms.

(VI-5) The food according to the above-described item (VI-4), in which when the carbon atom of ring A to which X is bonded in the cyclic compound is denoted by $C^1$; the carbon atom of ring A to which $R^2$ is bonded is denoted by $C^2$; the carbon atom of ring A to which $R^3$ is bonded is denoted by $C^3$; the carbon atom of ring A to which $R^4$ is bonded is denoted by $C^4$; the carbon atom of ring A to which $R^5$ is bonded is denoted by $C^5$; and the carbon atom of ring A to which $R^6$ is bonded is denoted by $C^6$, a combination in which the carbon atom is an asymmetric carbon atom is one selected from the group consisting of the following (a) to (h):

(a) $C^1$
(b) $C^2$
(c) $C^3$
(d) $C^4$
(e) $C^1$ and $C^4$
(f) $C^3$ and $C^4$
(g) $C^1$, $C^3$, and $C^4$
(h) $C^3$, $C^4$, and $C^5$ (VI-6) The food according to the above-described item (VI-1), in which the cyclic compound or the derivative thereof is 3-dehydroquinate, 3-dehydroshikimic acid, shikimic acid, chorismic acid, or prephenic acid.

(VI-7) The food according to any one of the above-described items (VI-1) to (VI-6), in which the microorganism is *Escherichia coli, Bacillus subtilis, Staphylococcus aureus*, a *Corynebacterium*, an Actinomycete, a Cyanobacterium, a methanogenic bacterium, a halophilic bacterium, a heat-resistant acidophilic bacterium, an acid-fast bacterium, a fungus, a yeast, or a transformant thereof.

(VI-8) The food according to any one of the above-described items (VI-1) to (VI-7), in which a raw material for the plant-derived saccharide is an inedible biomass resource.

(VI-9) A food additive containing at least one of a cyclic compound derived from a plant-derived saccharide and a microorganism and a derivative of the cyclic compound.

(VI-10) A method for producing a cyclic compound or a derivative thereof, which is used as a food or a food additive, the method including:
preparing a culture liquid including a plant-derived saccharide and a microorganism so as to produce at least one of the cyclic compound and a derivative thereof;
concentrating the culture liquid to obtain a concentrated liquid; and
collecting at least one of the cyclic compound and a derivative thereof from the concentrated liquid by a crystallization method, a precipitation method, an extraction method, a sublimation purification method, or a distillation method.

According to the present embodiment, a safer food and a safer food additive, which do not include petroleum-derived impurities, can be provided.

Furthermore, according to the present embodiment, a safer food or a safer food additive, which does not include petroleum-derived impurities, can be efficiently produced.

In the following description, the food, the food additive, and the method for producing a cyclic compound or a derivative thereof according to the present embodiment will be described in detail based on the suitable embodiments.

<<Food and Food Additive>>

The present inventors conducted a thorough investigation, and as a result, the inventors found that a food or a food additive, which does not include petroleum-derived impurities, can be provided by incorporating at least one of a cyclic compound derived from a plant-derived saccharide and a microorganism and a derivative of the cyclic compound. At this time, it was found that it is preferable to produce the cyclic compound or the derivative thereof by a bioprocess using a plant-derived saccharide (raw material) and a microorganism.

That is, the food of the present embodiment contains at least one of a cyclic compound derived from a plant-derived saccharide and a microorganism and a derivative of the cyclic compound. In other words, the food of the present embodiment contains at least one of a cyclic compound produced by a reaction (bioprocess) between a plant-derived saccharide and a microorganism, and a derivative of the cyclic compound.

As a result, a food that does not include petroleum-derived impurities can be provided. Such a food is highly safe compared to foods containing petroleum-derived impurities.

Furthermore, at least one of a cyclic compound derived from a plant-derived saccharide and a microorganism and a derivative of the cyclic compound is also used as a food additive.

As a result, a food additive that contains at least one of a cyclic compound and a derivative thereof but does not include petroleum-derived impurities, can be provided. Such a food additive is highly safe compared to food additives containing petroleum-derived impurities.

Examples of the cyclic compound included in a food or a food additive as such include compounds in which the ring-constituting atoms include a carbon atom, a nitrogen atom, an oxygen atom, a sulfur atom, and the like, and the number of ring members is about 3 to 12. Furthermore, the bond between the atoms constituting the ring may be a single bond or may be a double bond.

Such a cyclic compound is not limited but is preferably a compound represented by the following General Formula (1):

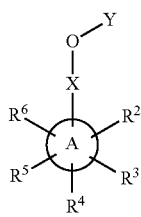

(1)

wherein in the General Formula (1), a ring A represents a 5-membered ring of a saturated ring, a partially saturated ring, or an aromatic ring, or a 6-membered ring of a saturated ring, a partially saturated ring, or an aromatic ring; X represents a single bond or a bond including one or more carbons; Y represents a hydrogen atom or an alkyl group; and $R^2$ to $R^6$ (in a case where the ring A is a 5-membered ring, $R^2$ to $R^5$) each independently represent a hydrogen atom, a hydroxyl group, an amino group, an alkoxy group, a carboxyl group, or a carbonyl group.

Examples of the 5-membered ring of a saturated ring, a partially saturated ring, or an aromatic ring include a furan structure, a thiophene structure, a pyrrole structure, a pyrrolidine structure, a tetrahydrofuran structure, a 2,3-dihydrofuran structure, a pyrazole structure, an imidazole structure, an oxazole structure, an isoxazole structure, a thiazole structure, and an isothiazole structure.

Examples of the 6-membered ring of a saturated ring include a hydrocarbon-based saturated ring such as a cyclohexane structure; a nitrogen-containing saturated ring such as a piperidine structure, a piperazine structure, a triazinane structure, a tetrazinane structure, a pentazinane structure, or a quinuclidine structure; an oxygen-containing saturated ring such as a tetrahydropyran structure or a morpholine structure; and a sulfur-containing saturated ring such as a tetrahydrothiopyran structure.

Examples of the 6-membered ring of a partially saturated ring include a hydrocarbon-based partially saturated ring such as a cyclohexene structure or a cyclohexadiene structure; a nitrogen-containing partially saturated ring such as a piperidine structure; an oxygen-containing partially saturated ring such as a pyran structure; and a sulfur-containing partially saturated ring such as a triazine structure.

Examples of the 6-membered ring of an aromatic ring include a hydrocarbon-based aromatic ring such as a benzene structure; and a nitrogen-containing aromatic ring (nitrogen-containing unsaturated ring) such as a pyridine structure, a pyridazine structure, a pyrimidine structure, a pyrazine structure, a triazine structure, a tetrazine structure, or a pentazine structure.

X represents s a single bond or a bond including one or more carbons (the number of carbon atoms is 1 or more).

When X is a single bond, an oxygen atom is directly bonded to the ring-constituting atom of ring A.

On the other hand, examples of the bond including one or more carbons include a hydrocarbon group having 1 to 4 carbon atoms, an ether bond, an ester bond, an amide bond, a carbonyl group, and a vinylidene group, and the bond is considered to be one kind or a combination of two or more kinds among these.

Among these, the hydrocarbon group having 1 to 4 carbon atoms may be either a straight chain or a branched chain and may be either saturated or unsaturated. The hydrogen atom of the hydrocarbon group may be substituted with a substituent such as an alkyl group having 1 to 2 carbon atoms, a hydroxyl group, an amino group, a carboxyl group, or a halogen atom.

X may include any atom or atomic group, in addition to the above-mentioned bonds. For example, X may be an atomic group including a carbonyl group and a bond including one or more carbons.

Y represents a hydrogen atom or an alkyl group. The number of carbon atoms of the alkyl group is preferably adjusted to 1 to 12, and more preferably adjusted to 1 to 4.

In a case where ring A is a 6-membered ring, $R^2$ to $R^6$ each independently represent a hydrogen atom, a hydroxyl group, an amino group, an alkoxy group, a carboxyl group, or a carbonyl group. Furthermore, in a case where ring A is a 5-membered ring, $R^2$ to $R^5$ each independently represent a hydrogen atom, a hydroxyl group, an amino group, an alkoxy group, a carboxyl group, or a carbonyl group.

When any one of $R^2$ to $R^6$ in the case where ring A is a 6-membered ring, or any one of $R^2$ to $R^5$ in the case where ring A is a 5-membered ring, is a carbonyl group, a structure in which the ring-constituting atoms of ring A are carbon atoms and a double bond is present between one of the carbon atoms and the oxygen atom, is referred to as a carbonyl group.

In a case where ring A is a 6-membered ring, the carbon atoms constituting ring A may be independently such that any one of $R^2$ to $R^6$ is bonded to one carbon atom, or any two of them are bonded to one carbon atom. Furthermore, in a case where ring A is a 5-membered ring, the carbon atoms constituting ring A may be independently such that any one of $R^2$ to $R^5$ is bonded to one carbon atom, or any two of them are bonded to one carbon atom.

Specific examples of the cyclic compound include benzoic acid, phthalic acid, isophthalic acid, terephthalic acid, hemimellitic acid, trimellitic acid, trimesic acid, mellophanic acid, prehnitic acid, pyromellitic acid, phenylacetic acid, hydroxyphenylacetic acid, phenylbutyric acid (phenyl lactate), hydroxyphenylbutyric acid, phenylpyruvic acid, hydroxyphenylpyruvic acid, phenyllactic acid, hydroxyphenyllactic acid, anthranilic acid, hydroatropic acid, atropic acid, hydrocinnamic acid (coumaric acid), cinnamic acid, salicylic acid (2-hydroxybenzoic acid), m-salicylic acid (3-hydroxybenzoic acid), p-salicylic acid (4-hydroxybenzoic acid), methoxybenzoic acid, aminobenzoic acid, hydroxybenzoic acid, pyrocatechuic acid (2,3-dihydroxybenzoic acid), β-resorcylic acid (2,4-dihydroxybenzoic acid), gentisic acid (2,5-dihydroxybenzoic acid), γ-resorcylic acid (2,6-dihydroxybenzoic acid), protocatechuic acid (3,4-dihydroxybenzoic acid), α-resorcylic acid (3,5-dihydroxybenzoic acid), trihydroxybenzoic acid, vanillic acid (4-hydroxy-3-methoxybenzoic acid), isovanillic acid (3-hydroxy-4-methoxybenzoic acid), veratric acid, gallic acid, syringic acid, asaronic acid, mandelic acid, vanillylmandelic acid, anisic acid, homoprotocatechuic acid, homovanillic acid, homoisovanillic acid, homoveratric acid, homophthalic acid, homoisophthalic acid, homoterephthalic acid, phthalonic acid, isophthalonic acid, terephthalonic acid, atrolactic acid, tropic acid, melilotic acid, phloretic acid, dihydrocaffeic acid, hydroferulic acid, hydroisoferulic acid, umbellic acid, caffeic acid (coffee acid), ferulic acid, isoferulic acid, sinapic acid, syringic acid, dehydroquinic acid, dehydroshikimic acid, shikimic acid, chorismic acid, L-tryptophan, L-tyrosine, prephenic acid, arogenic acid, and L-phenylalanine.

Furthermore, other specific examples of the cyclic compound include flavonoid, lignan, chalcone, stilbenoid, alkaloid, curcuminoid, terpenoid, saponin, various glucosides, polyphenols such as various polyphenol-based aromatic compounds, amino acids, and vitamins.

Among these, examples of flavonoid include anthocyanidins such as aurantinidin, cyanidin, delphinidin, europinidin, luteolinidin, pelargonidin, malvidin, peonidin, petunidin, and rosinidin; anthocyanins such as procyanidin; flavanones such as naringenin, eriocitrin, pinocembrin, and eriodictyol; flavans such as catechin; flavones such as apigenin, luteolin, baicalein, and chrysin; flavonols such as quercetin and kempferol; isoflavonoids such as isoflavon, isoflavane, isoflavanediol, and genistein; neoflavonoid, biflavonoid, aurone, prenylflavonoid, and O-methylated flavonoid.

Examples of lignans include pinoresinol, lariciresinol, secoisolariciresinol, matairesinol, hydroxymatairesinol, syringaresinol, sesamin, arctigenin, sesaminol, podophyllotoxin, and steganacin.

Examples of stilbenoid include aglycone such as piceatannol, pinosylvin, pterostilbene, resveratrol, 4'-methoxyresveratrol, pinostilbene, and pisiatanol; and oligomers such as α-viniferin, ampelopsin A, ampelopsin E, diptoindonesin C-Kawan, diptoindonesin F-Damarbua, s-viniferin, flexosol A, gnetin H, hemsleyanol D, hopeaphenol, diptoindonesin B, and vaticanol B.

Examples of curcuminoid include curcumin and shogaol.

Examples of terpenoid include carotenoids such as lutein, vitamin A, vitamin E, and β-carotene; and steroids such as sitosterol.

Examples of various glucosides include phenol glucosides such as salicin, β-glucogallin, salicylic acid glucoside, salidroside, gastrodin, populin, phlorizin, and arbutin; coumarin glucosides such as esculin; flavonoid glucosides such as hesperidin and rutin; and stilbenoid glucosides such as astringin, piceid, and diptoindonesin A.

Examples of various polyphenol-based aromatic compounds include tyrosol, hydroxytyrosol, esculetin, phloretin, rosmarinic acid, salvianic acid A, reticulin, paracoumaryl alcohol, coniferyl alcohol, and caffeyl alcohol.

Examples of amino acids include phenylalanine and tyrosine.

Examples of vitamins include vitamin A, vitamin D, and vitamin E.

Furthermore, other specific examples of the cyclic compound include an aromatic compound, an alicyclic compound, an aliphatic compound, and a heterocyclic compound.

Among these, examples of the aromatic compound include vanillin, 2-phenylethanol, phenylacetic acid, cinnamic alcohol, isoeugenol, ferulic acid, 4-aminobenzoic acid, anethole, estragole, methyl anthranilate, methyl cinnamate, ethyl cinnamate, phenylacetaldehyde, cinnamic aldehyde, cinnamyl acetate, resorcin, 4-vinylphenol, 4-vinyl-2-methoxyphenol, 3,4-dihydroxystyrene, dopamine, levodopa, hydroquinone, coumarin, 7-hydroxycoumarin, 4-hydroxycoumarin, and xiamenmycin A.

Examples of the alicyclic compound include carveol, perillyl alcohol, borneol, methyl jasmonate, 1,8-cineol, L-menthone, valencene, nootkatone, α-pinene, camphene, L-carvone, perillyl aldehyde, myrtenal, L-menthyl acetate, and β-ionone.

Examples of the aliphatic compound include cis-3-hexenol, cis-3-hexenyl acetate, acetoin, nerol, farnesol, arginine, and muconic acid.

Examples of the heterocyclic compound include niacin, niacinamide, maltol, and indole.

On the other hand, regarding the derivative of the cyclic compound, for example, an ester, an acid anhydride, an amide, an acid halide, a salt, and the like of the above-mentioned compound; or all compounds derived from the cyclic compound may be mentioned.

Among the cyclic compounds such as described above, the cyclic compound represented by General Formula (1) is more preferably at least one selected from the group consisting of 2-hydroxybenzoic acid, 3-hydroxybenzoic acid, 4-hydroxybenzoic acid, 2,3-dihydroxybenzoic acid, 2,4-dihydroxybenzoic acid, 2,5-dihydroxybenzoic acid, 2,6-dihydroxybenzoic acid, 3,4-dihydroxybenzoic acid, and 3,5-dihydroxybenzoic acid. By using these, a safer food or food additive having various efficacies can be realized.

The molecular weight of the cyclic compound or the derivative thereof is not limited; however, the molecular weight is preferably 120 to 1000, and more preferably 130 to 800.

Furthermore, in a case where ring A of the cyclic compound represented by General Formula (1) is a 5-membered ring of a saturated ring or a partially saturated ring, in which all the ring-constituting atoms are carbon atoms, it is preferable that one or more of the carbon atoms of ring A to which $R^2$ to $R^5$ and X are bonded are asymmetric carbon atoms. In a case where ring A of the cyclic compound represented by General Formula (1) is a 6-membered ring of a saturated ring or a partially saturated ring, in which all the ring-constituting atoms are carbon atoms, it is preferable that one or more of the carbon atoms of ring A to which $R^2$ to $R^6$ and X are bonded are asymmetric carbon atoms.

In such a case, the cyclic compound is a stereoisomer, and thereby a meaningful food or food additive can be realized. Furthermore, by producing such a cyclic compound from a plant-derived saccharide, a food or food additive including a specific stereoisomer with high purity can be obtained. That is, a food or food additive including a specific stereoisomer with high purity and having a low content percentage of other stereoisomers can be obtained. Such a food or food additive is useful from the viewpoint that a food or food additive having excellent safety and efficacy can be realized. Furthermore, since a complicated production step for removing unnecessary stereoisomers is not required, reduction of the production cost can be attempted.

Furthermore, when the carbon atom of ring A to which X is bonded in the cyclic compound represented by General Formula (1) is denoted by $C^1$; the carbon atom of ring A to which $R^2$ is bonded is denoted by $C^2$; the carbon atom of ring A to which $R^3$ is bonded is denoted by $C^3$; the carbon atom of ring A to which $R^4$ is bonded is denoted by $C^4$; the carbon atom of ring A to which $R^5$ is bonded is denoted by $C^5$; and the carbon atom of ring A to which $R^6$ is bonded is denoted by $C^6$, it is preferable that the combination in which these carbon atoms are asymmetric carbon atoms is any one selected from the group consisting of the following (a) to (h):

$C^1$ to $C^6$ may be respectively different carbon atoms, or any two of $C^1$ to $C^6$ may be the same carbon atom.
(a) $C^1$
(b) $C^2$
(c) $C^3$
(d) $C^4$
(e) $C^1$ and $C^4$
(f) $C^3$ and $C^4$
(g) $C^1$, $C^3$, and $C^4$
(h) $C^3$, $C^4$, and $C^5$ The following General Formula (2) is a formula in which the indications of $C^1$ to $C^6$ have been added to the cyclic compound represented by General Formula (1).

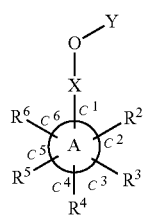

(2)

wherein in the General Formula (2), ring A represents a 5-membered ring of a saturated ring, a partially saturated ring, or an aromatic ring, or a 6-membered ring of a saturated ring, a partially saturated ring, or an aromatic ring; X represents a single bond or a bond including one or more carbons; Y represents a hydrogen atom or an alkyl group; $R^2$ to $R^6$ (in a case where the ring A is a 5-membered ring, $R^2$ to $R^5$) each independently represent a hydrogen atom, a hydroxyl group, an amino group, an alkoxy group, a carboxyl group, or a carbonyl group; and $C^1$ to $C^6$ are each a carbon atom as a ring-constituting atom of ring A.

In such a case, the cyclic compound is a stereoisomer, and thereby a more meaningful food or food additive can be realized. By producing such a cyclic compound from a plant-derived saccharide, a food or food additive including a specific stereoisomer with high purity, which is one selected from the group consisting of the above-described (a) to (h), can be obtained. That is, a food or food additive including a specific stereoisomer with high purity and having a low content percentage of other stereoisomers can be obtained. Such a food or food additive is useful from the viewpoint that a food or food additive having excellent safety and efficacy can be realized. Furthermore, since any complicated production steps associated with the removal of unnecessary stereoisomers can be cut down, the production cost can be reduced.

The cyclic compound and a derivative thereof according to the present embodiment are compounds represented by the above-described General Formula (2), and in addition, it is preferable that the cyclic compound is 3-dehydroquinate, 3-dehydroshikimic acid, shikimic acid, chorismic acid, or prephenic acid. All of these compounds can be produced from plant-derived saccharides and are also useful as foods or food additives. Therefore, by using these compounds produced from plant-derived saccharides, a food or a food additive, which has superior efficacy and is safer, can be realized.

The structures of these cyclic compounds are represented by the following formulae.

3-Dehydroquinate

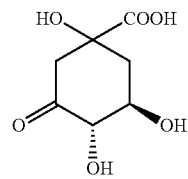 [SMILES: O=C1CC(O)(C(=O)O)C[C@@H](O)[C@@H]1O]

3-Dehydroshikimic Acid

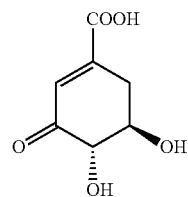 [SMILES: O=C(O)C1=CC(=O)[C@@H](O)[C@H](O)C1]

Shikimic Acid

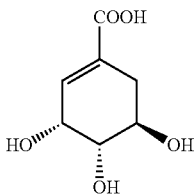

Chorismic Acid

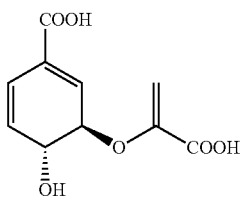 [SMILES: C=C(O[C@@H]1C=C(C(=O)O)C=C[C@H]1O)C(=O)O]

Prephenic Acid

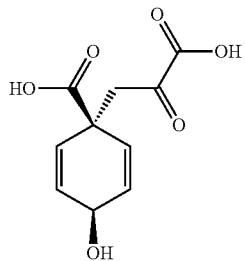 [SMILES: O=C(O)C(=O)C[C@]1(C(=O)O)C=C[C@@H](O)C=C1]

The food containing at least one of a cyclic compound such as described above and a derivative thereof is not limited as long as it is a commonly eaten food or drink. Examples include oral compositions such as gums and candies; fishery paste products such as kamaboko and chikuwa; livestock products such as sausage and ham; Western confectionery; Japanese confectionery; noodles such as Chinese noodles, udon noodles, and buckwheat noodles; seasonings such as sauces, soy sauce, and gravy; side dishes, juices, and soups.

In addition, in the case of providing supplements or health foods, the food may be provided in the form of capsules or tablets as is the case of pharmaceuticals or may be provided in the form of being added to various foods such as beverages, seasonings, and confectionery. Examples of functions of the supplements or health foods include functions of preventing or ameliorating at least one of antioxidant action, anti-arteriosclerosis, anti-hypertension, radical capture activity, enzyme inhibitory activity, restoration of cellular tissue on the inner side of the skin, regeneration of capillaries, enhancement of resistance to bacteria, regeneration of red blood cells, blood pressure regulation, immunological enhancement, anticancer, antiviral, suppression of blood glucose level elevation, liver function improvement, intestinal flora improvement, bowel movement improvement, lipid metabolism improvement, antioxidant function enhancement, physical strength enhancement, promotion of skin beautification, hair restoration, blood vessel-related diseases (arteriosclerosis, hypertension, heart disease), neurodegenerative diseases, ischemic cerebrovascular disorders, ischemic heart disease, inflammatory bowel disease, and eye diseases.

Furthermore, examples of a food additive containing at least one of a cyclic compound and a derivative thereof include additives designated under the Food Sanitation Law. Examples include a preservative, a sweetener, a colorant, and a food flavor (flavor). Among these, for example, protocatechuic acid is used as a sweetness enhancer. By using such a sweetness enhancer, the sweetness intensity of the food can be increased, and therefore, the amount of addition of sugar can be relatively reduced. As a result, the food has added value from the viewpoint of low sugar and can realize a safe food. Furthermore, regarding the function of food flavors, for example, flavoring, perfuming, flavor correction, sweetness enhancement, acidity and bitterness reduction, and promotion of appetite may be mentioned.

Examples of the form of the food additive include a water-soluble liquid, an oil-soluble liquid, an emulsified body (emulsion), and a powder.

<<Method for Producing Cyclic Compound or Derivative Thereof>>

The above-mentioned cyclic compound or a derivative thereof is produced by a bioprocess that uses a microorganism, by using a plant-derived saccharide as a raw material. That is, the above-mentioned cyclic compound or a derivative thereof is derived from a plant-derived saccharide and a microorganism.

Examples of the plant-derived saccharide include, but are not limited to, a monosaccharide, a polysaccharide, and a mixture thereof.

Examples of the monosaccharide include, but are not limited to, saccharides that can be treated with transformants of microorganisms that will be described later. Examples of such a saccharide (monosaccharide) include tetrose (C4 sugar), pentose (C5 sugar), hexose (C6 sugar), and heptose (C7 sugar), from the viewpoint of enhancing the phenol productivity of the transformant. Among these, the monosaccharide is preferably at least one selected from the group consisting of arabinose, xylose, glucose, mannitol, fructose, mannose, galactose, and sucrose. Furthermore, such a saccharide may be used alone, or a plurality thereof may be used in combination as a mixed sugar.

A polysaccharide is a polymer of monosaccharides. The average degree of polymerization of the polysaccharide is not limited; however, from the viewpoint of enhancing the productivity in a bioprocess using a microorganism, the average degree of polymerization is preferably equal to or more than 2 and equal to or less than 100, and more preferably equal to or more than 2 and equal to or less than 50. Furthermore, the polysaccharide may be used singly, or a plurality thereof may be used in combination. Examples of the polysaccharide include maltose, lactose, cellobiose, xylobiose, trehalose, acarbose, stachyose, fructooligosaccharide, galactooligosaccharide, and mannan oligosaccharide.

It is preferable that the plant-derived saccharide is produced from a non-edible biomass resource. In other words, it is preferable that the raw material of the plant-derived saccharide is an inedible biomass resource.

Regarding the biomass resource, various biomass resources can be used as long as they include at least monosaccharides or polysaccharides, from the viewpoint of obtaining saccharides such as mentioned above. Examples of the biomass resource include vegetation resources represented by weeds generated from urban areas or cultivated lands and lumber from thinning in forest production areas; waste cellulose, waste starch, and waste molasses collected as process residue or waste materials in the general food industry; pomace of sugarcane in the sugar industry; and sake lees and shochu lees in the sake brewing industry, and these can be used singly or in combination of a plurality thereof. Furthermore, a processed article can also be used as the biomass resource.

By saccharifying such a biomass resource, the plant-derived saccharide can be obtained. Such a plant-derived saccharide is preferably a cellulose-derived saccharide obtained by saccharifying waste cellulose, and more preferably a cellulose-derived mixed sugar. In the following description, a process for producing a cyclic compound or a derivative thereof by using a plant-derived saccharide as a raw material and using a microorganism will be described in detail.

The process using a microorganism, which uses a plant-derived saccharide as a raw material, is a process having obtaining a culture liquid including at least one of the cyclic compound and a derivative thereof produced by a microorganism by using the plant-derived saccharide as a raw material (produced by conversion of the plant-derived saccharide by the microorganism); concentrating the culture liquid to obtain a concentrated liquid; and collecting at least one of the cyclic compound and a derivative thereof from the concentrated liquid by a crystallization method, a precipitation method, an extraction method, a sublimation purification method, or a distillation method. By performing such a process, at least one of the cyclic compound and a derivative thereof can be efficiently obtained. Furthermore, according to such a process using a microorganism, a cyclic compound or a derivative thereof is produced as a result of a reaction between a raw material and a microorganism.

Therefore, by limiting the types of the raw material and the microorganism (for example, limiting the raw material to a plant-derived saccharide and limiting the type of the microorganism to a bacterium), a cyclic compound or a derivative thereof can be efficiently obtained. Such an effect can be notably exhibited by further limiting the types of the raw material and the microorganism (for example, limiting the raw material to a cellulose-derived mixed sugar and limiting the type of the bacterium). In this regard, the process is different from a process that does not use a microorganism (for example, a process that uses an extract from a plant). From this point of view, a cyclic compound and a derivative thereof derived from a plant-derived saccharide and a microorganism can be referred to as the cyclic compound and the derivative thereof (excluding plant extract-derived compounds).

With regard to the bioprocess, the collection rate of the cyclic compound and a derivative thereof can be enhanced by appropriately selecting the microorganism, the medium, the culturing facility, and the culture conditions.

<Preparing Culture Liquid>

First, a culture liquid including a raw material, a microorganism, a medium, and the like is prepared. At least one of a cyclic compound and a derivative thereof is produced by culturing the microorganism in this culture liquid and reacting the raw material or the like with the microorganism (by a bioprocess).

The type of the microorganism is not limited as long as the microorganism can produce the cyclic compound and a derivative thereof with high efficiency. Generally, the microorganism is selected according to the purpose from bacteria such as *Escherichia coli, Bacillus subtilis, Staphylococcus aureus*, and *Corynebacterium glutamicum*; Actinomycetes such as the genus *Streptomyces* (*Streptomyces griseus*); Cyanobacteria such as the genus *Microcystis* (*Microcystis aeruginosa*); archaebacteria such as methanogenic bacteria (*Methanobacterium thermoautotrophicum*), halophilic bacteria (*Halobacterium salinarum*), thermophilic acidophilic bacteria (*Sulfolobus acidocaldarius*), heat-resistant acidophilic bacteria (*Alicyclobacillus acidoterrestris*), and acid-fast bacterium; molds such as *Aspergillus oryzae*; and yeasts such as *Saccharomyces cerevisiae*, and transformants of these obtainable by known methods are utilized as necessary.

Regarding the medium, any medium that is usually used for culturing microorganisms may be applied. The medium includes medium components in order to prepare an environment necessary for the growth of microorganisms. It is preferable that the medium components contain appropriate amounts of a carbon source, a nitrogen source, inorganic salts, or other nutrients according to the type of the microorganism used. Therefore, it is preferable that the culture liquid before the bioprocess includes a raw material, a microorganism, and medium components.

Examples of the carbon source include carbohydrates or sugar alcohols, such as glucose, fructose, sucrose, mannose, maltose, mannitol, xylose, arabinose, galactose, starch, molasses, sorbitol, and glycerin; organic acids such as acetic acid, citric acid, lactic acid, fumaric acid, maleic acid, and gluconic acid; and alcohols such as ethanol and propanol. Regarding the carbon source, these may be used singly, or two or more kinds thereof may be mixed and used.

Examples of the nitrogen source include inorganic or organic ammonium compounds such as ammonium chloride, ammonium sulfate, ammonium nitrate, and ammonium acetate; urea, aqueous ammonia, sodium nitrate, and potassium nitrate. Furthermore, nitrogen-containing organic compounds such as corn steep liquor, meat extract, peptone, NZ-amine, protein hydrolysates, and amino acids, and the like can also be utilized. Regarding the nitrogen source, these may be used singly, or two or more kinds thereof may be mixed and used.

Examples of the inorganic salts include monopotassium phosphate, dipotassium phosphate, magnesium sulfate, sodium chloride, ferrous nitrate, manganese sulfate, zinc sulfate, cobalt sulfate, and calcium carbonate. Regarding the inorganic salts, these may be used singly, or two or more kinds thereof may be mixed and used.

Examples of the nutrients include meat extract, peptone, polypeptone, yeast extract, dried yeast, corn steep liquor, skim milk powder, defatted soybean hydrochloric acid hydrolysate, extracts of animals and plants or microbial cells, and degradation products thereof. In addition, vitamins can also be added to the medium as necessary. Examples of the vitamins include biotin, thiamine (vitamin B1), pyridoxine (vitamin B6), pantothenic acid, inositol, and nicotinic acid.

The culturing facility may be any of a batch type, a fed-batch type, or a continuous type; however, in the case of assuming multiproduct production, a batch type is preferable. Furthermore, in general, a seed culture method in which expansion culture is performed gradually by starting from flask-scale culture is often employed, and a group of incubators whose sizes differ by several stages are used as one set according to the production scale. Regarding the culture conditions, the medium temperature is preferably about 15° C. to 45° C., and the pH of the medium is preferably about 6 to 8. In addition, parameters such as the aeration method and aeration amount to the culture tank, the agitation method, the speed of rotation, the shape of stirring blade, and the culturing time are appropriately set according to the scale and specifications of the culturing facility, and the type and concentration of the microorganism used, and the culturing process is appropriately regulated by real-time monitoring.

<Concentration, and Isolation and Purification>

The culture liquid obtainable by a bioprocess can be prepared in a state of containing the cyclic compound or a derivative thereof at a suitable concentration when the microbial growth environment is appropriately selected. A collecting process including a concentration, and an isolation and purification for the culture liquid is applied for the purpose of selectively and efficiently collecting the cyclic compound or a derivative thereof from the culture liquid prepared in this manner. According to such a method, a cyclic compound or a derivative thereof can be efficiently produced.

The concentration is carried out for the purpose of increasing the content concentration of at least one of the cyclic compound and a derivative thereof in the culture liquid obtainable after the bioprocess and collecting the target compound in high purity with high yield in the subsequent isolation and purification. In the following description, the concentration will be described.

The culture liquid after the bioprocess includes, in addition to at least one of the cyclic compound and a derivative thereof produced by the bioprocess, a carbon source, a nitrogen source, inorganic salts, nutrients, and the like as medium components and also contains organic acids created as by-products as well as amino acids and salts thereof. Incidentally, 70% to 99% of the total weight of the culture liquid after the bioprocess is usually water. Therefore, in the concentration, it is desirable that water can be efficiently removed without deteriorating or depleting the cyclic compound or a derivative thereof, and without further increasing the amount of by-products-concomitantly with concentration. To this end, chemical engineering techniques such as heating concentration, reduced pressure distillation, solvent extraction, solid extraction, and membrane separation can be applied; however, reduced pressure concentration is more suitably used so as to avoid deterioration or depletion caused by heat or oxidation of the cyclic compound or a derivative thereof during the concentration, and to reduce the input amount of heat energy concomitant with water removal.

The isolation and purification is carried out for the purpose of selectively collecting at least one of the cyclic compound and a derivative thereof from the concentrated liquid obtainable by the concentration.

In the isolation and purification, for example, various chemical engineering techniques such as steam distillation, precision fractional distillation, temperature crystallization, acid crystallization, salting out, reprecipitation, sublimation, column purification, extraction, and membrane separation, can be applied. A suitable method is selected in consideration of the properties of the target compound and the properties of impurities and by-products to be removed. Cyclic compounds vary in terms of the properties depending on the type and number of substituents; however, in a case where the cyclic compound or a derivative thereof is solid at room temperature and the water-solubility of impurities and by-products is relatively high, a crystallization method (temperature crystallization or acid crystallization) is suitably used.

<Processing into Food or Food Additive>

A food or a food additive is obtained by processing the cyclic compound or a derivative thereof produced as described above, as necessary. An example of such processing may be addition of optional components. The food or food additive of the present embodiment may include any other components to the extent that the effect of the present embodiment is not impaired.

Examples of the other components include sugar, condensed milk, wheat flour, shortening, table salt, glucose, chicken egg, butter, margarine, starch syrup, calcium, iron, seasonings, spices, oils (animal and vegetable oils, mineral oils, ester oils, wax oils, silicone oils, higher alcohols, phospholipids, fatty acids, and the like), surfactants (anionic, cationic, amphoteric, or nonionic surfactants), vitamins (vitamin A group, vitamin B group, folic acids, nicotinic acids, pantothenic acids, biotins, vitamin C group, vitamin D group, vitamin E group, other ferulic acid, γ-oryzanol, and the like), ultraviolet absorbers (p-aminobenzoic acid, anthranilic acid, salicylic acid, coumarin, benzotriazole, tetrazole, imidazoline, pyrimidine, dioxane, furan, pyrone, camphor, nucleic acid, allantoin or derivatives thereof, amino acid-based compounds, shikonin, baicalin, baicalein, berberine, and the like), antioxidants (stearic acid esters, nordihydroguaiaretic acid, dibutylhydroxytoluene, butylhydroxyanisole, parahydroxyanisole, propyl gallate, sesamol, sesamolin, gossypol, and the like), thickeners (hydroxyethyl cellulose, ethyl cellulose, carboxyethyl cellulose, methyl cellulose, carboxymethyl cellulose, sodium carboxymethyl cellulose, hydoxypropyl cellulose, nitrocellulose, polyvinyl alcohol, polyvinyl methyl ether, polyvinylpyrrolidone, polyvinyl methacrylate, polyacrylic acid salts, carboxyvinyl polymers, gum arabic, tragacanth gum, agar, casein, dextrin, gelatin, pectin, starch, alginic acid or salts thereof, and the like), moisturizers (propylene glycol, 1,3-butylene glycol, polyethylene glycol, glycerin, 1,2-pentanediol, hexylene glycol, octylene glycol, chondroitin sulfate or salts thereof, hyaluronic acid or salts thereof, sodium lactate, and the like), lower alcohols, polyhydric alcohols, water-soluble polymers, pH adjusting agents, antiseptic/antifungal agents, colorants, flavors, refreshing agents, stabilizers, animal/plant extracts, animal/plant proteins or degradation products thereof, animal/plant polysaccharides or degradation products thereof, animal/plant glycoproteins or degradation products thereof, microbial culture metabolic components, blood flow promoters, anti-phlogistic agents, anti-inflammatory agents, anti-allergic agents, cell activators, amino acids or salts thereof, keratolytic agents, astringent agents, wound healing agents, foam increasing agents, oral agents, deodorizers/deodorants, and emulsifiers. These can be used singly or in combination of two or more kinds thereof.

The food of the present embodiment may be in any form and is not limited.

Thus, the food or food additive of the present embodiment has been described above; however, specific examples of the food or food additive are not limited to those described above and may be in any form.

Fifth Embodiment

The present embodiment relates to a flavor and a method for producing a cyclic compound or a derivative thereof.

It is known that cyclic compounds having a specific structure are used as flavors. For example, Patent Document 9 (Japanese Unexamined Patent Publication No. 8-92589) discloses a flavor composition containing an alcohol and an aromatic aldehyde.

However, cyclic compounds such as the above-described aromatic aldehydes are usually obtained from petroleum. In such a case, a petroleum-derived cyclic compound (chemical product) that can be collected by fractional distillation refining of petroleum is a so-called basic compound having a simple chemical structure. On the other hand, a high value-added compound having a more complicated chemical structure has to be derived from this basic compound through a synthesis process. In this case, unless petroleum is fractionated and refined at a high level while disregarding the production cost, various isomers derived from raw materials and synthesis processes, trace components derived from catalysts, ionic components, mineral components, and the like may remain in the petroleum-derived chemical products. It cannot be said that these impurities included in the petroleum-derived chemical products are preferable from the viewpoint of safety to the human body.

An object of the present embodiment is to provide a safer flavor that does not include petroleum-derived impurities. Another object of the present invention is to provide a method for producing a cyclic compound or a derivative thereof, which can be used as a flavor.

Such an object is achieved by the present embodiment described in the following (V-1) to (V-9).

(V-1) A flavor containing at least one of a cyclic compound derived from a plant-derived saccharide and a microorganism and a derivative thereof.

(V-2) The flavor according to the above-described (V-1), in which the cyclic compound is a compound represented by the following General Formula (1):

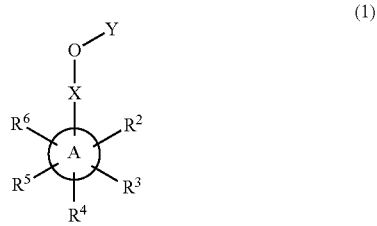

wherein in the General Formula (1), a ring A represents a 5-membered ring of a saturated ring, a partially saturated ring, or an aromatic ring, or a 6-membered ring of a saturated ring, a partially saturated ring, or an aromatic ring; X represents a single bond or a bond including one or more carbons; Y represents a hydrogen atom or an alkyl group; and $R^2$ to $R^6$ (in a case where the ring A is a 5-membered ring, $R^2$ to $R^5$) each independently represent a hydrogen atom, a hydroxyl group, an amino group, an alkoxy group, a carboxyl group, or a carbonyl group.

(V-3) The flavor according to the above-described item (V-2), in which the cyclic compound is at least one selected from the group consisting of 2-hydroxybenzoic acid, 3-hydroxybenzoic acid, 4-hydroxybenzoic acid, 2,3-dihydroxybenzoic acid, 2,4-dihydroxybenzoic acid, 2,5-dihydroxybenzoic acid, 2,6-dihydroxybenzoic acid, 3,4-dihydroxybenzoic acid, and 3,5-dihydroxybenzoic acid.

(V-4) The flavor according to the above-described item (V-2), in which when ring A of the cyclic compound is a 5-membered ring of a saturated ring or a partially saturated ring, in which all the ring-constituting atoms are carbon atoms, one or more of the carbon atoms of ring A to which $R^2$ to $R^5$ and X are bonded are asymmetric carbon atoms, and when ring A of the cyclic compound is a 6-membered ring of a saturated ring or a partially saturated ring, in which all the ring-constituting atoms are carbon atoms, one or more of the carbon atoms of ring A to which $R^2$ to $R^6$ and X are bonded are asymmetric carbon atoms.

(V-5) The flavor according to the above-described item (V-4), in which when the carbon atom of ring A to which X is bonded in the cyclic compound is denoted by $C^1$; the carbon atom of ring A to which $R^2$ is bonded is denoted by $C^2$; the carbon atom of ring A to which $R^3$ is bonded is denoted by $C^3$; the carbon atom of ring A to which $R^4$ is bonded is denoted by $C^4$; the carbon atom of ring A to which $R^5$ is bonded is denoted by $C^5$; and the carbon atom of ring A to which $R^6$ is bonded is denoted by $C^6$, the combination in which the carbon atoms are asymmetric carbon atoms is one selected from the group consisting of the following (a) to (h):

(a) $C^1$
(b) $C^2$
(c) $C^3$
(d) $C^4$
(e) $C^1$ and $C^4$
(f) $C^3$ and $C^4$
(g) $C^1$, $C^3$, and $C^4$
(h) $C^3$, $C^4$, and $C^5$ (V-6) The flavor according to the above-described item (V-1), in which the cyclic compound or the derivative thereof is 3-dehydroquinate, 3-dehydroshikimic acid, shikimic acid, chorismic acid, or prephenic acid.

(V-7) The flavor according to any one of the above-described items (V-1) to (V-6), in which the microorganism is Escherichia coli, Bacillus subtilis, Staphylococcus aureus, a Corynebacterium, an Actinomycete, a Cyanobacterium, a methanogenic bacterium, a halophilic bacterium, a heat-resistant acidophilic bacterium, an acid-fast bacterium, a fungus, a yeast, or a transformant thereof.

(V-8) The flavor according to any one of the above-described items (V-1) to (V-7), in which a raw material for the plant-derived saccharide is an inedible biomass resource.

(V-9) A method for producing a cyclic compound or a derivative thereof, which is used as a flavor, the method including:

preparing a culture liquid including a plant-derived saccharide and a microorganism so as to produce at least one of the cyclic compound and a derivative thereof;

concentrating the culture liquid to obtain a concentrated liquid; and collecting at least one of the cyclic compound and a derivative thereof from the concentrated liquid by a crystallization method, a precipitation method, an extraction method, a sublimation purification method, or a distillation method.

According to the present embodiment, a safer flavor that does not include petroleum-derived impurities can be provided.

Furthermore, according to the present embodiment, a safer flavor that does not include petroleum-derived impurities can be efficiently produced.

In the following description, the flavor and the method for producing a cyclic compound or a derivative thereof according to the present embodiment will be described in detail based on suitable embodiments.

<<Flavor>>

The present inventors conducted a thorough investigation, and as a result, the inventors found that a flavor that does not include petroleum-derived impurities can be provided by incorporating at least one of a cyclic compound derived from a plant-derived saccharide and a microorganism and a derivative of the cyclic compound. At this time, it was found that it is preferable to produce the cyclic compound or the derivative thereof by a bioprocess using a plant-derived saccharide (raw material) and a microorganism.

That is, the flavor of the present embodiment contains at least one of a cyclic compound derived from a plant-derived saccharide and a microorganism and a derivative of the cyclic compound. In other words, the flavor of the present embodiment contains at least one of a cyclic compound produced by a reaction (bioprocess) between a plant-derived saccharide and a microorganism and a derivative thereof.

As a result, a flavor that does not include petroleum-derived impurities can be provided. Such a flavor is highly safe compared to flavors containing petroleum-derived impurities.

Examples of the cyclic compound contained in the flavor include compounds in which the ring-constituting atoms are carbon atoms, nitrogen atoms, oxygen atoms, sulfur atoms, and the like, and the number of ring members is about 3 to 12. Furthermore, the bond between the atoms constituting the ring may be a single bond or may be a double bond.

Such a cyclic compound is not limited but is preferably a compound represented by General Formula (1) described above in the fourth embodiment. Then, the specific configuration of the compound represented by General Formula (1) can adopt the configuration mentioned above in the fourth embodiment.

Specific examples of the cyclic compound include benzoic acid, phthalic acid, isophthalic acid, terephthalic acid, hemimellitic acid, trimellitic acid, trimesic acid, mellophanic acid, prehnitic acid, pyromellitic acid, phenylacetic acid, hydroxyphenylacetic acid, phenylbutyric acid (phenyl lactate), hydroxyphenylbutyric acid, phenylpyruvic acid, hydroxyphenylpyruvic acid, phenyllactic acid, hydroxyphenyllactic acid, anthranilic acid, hydroatropic acid, atropic acid, hydrocinnamic acid (coumaric acid), cinnamic acid, salicylic acid (2-hydroxybenzoic acid), m-salicylic acid (3-hydroxybenzoic acid), p-salicylic acid (4-hydroxybenzoic acid), methoxybenzoic acid, aminobenzoic acid, hydroxybenzoic acid, pyrocatechuic acid (2,3-dihydroxybenzoic acid), β-resorcylic acid (2,4-dihydroxybenzoic acid), gentisic acid (2,5-dihydroxybenzoic acid), γ-resorcylic acid (2,6-dihydroxybenzoic acid), protocatechuic acid (3,4-dihydroxybenzoic acid), α-resorcylic acid (3,5-dihydroxybenzoic acid), trihydroxybenzoic acid, vanillic acid (4-hydroxy-3-methoxybenzoic acid), isovanillic acid (3-hydroxy-4-methoxybenzoic acid), veratric acid, gallic acid, syringic acid, asaronic acid, mandelic acid, vanillylmandelic acid, anisic acid, homoprotocatechuic acid, homovanillic acid, homoisovanillic acid, homoveratric acid, homophthalic acid, homoisophthalic acid, homoterephthalic acid, phthalonic acid, isophthalonic acid, terephthalonic acid, atrolactic acid, tropic acid, melilotic acid, phloretic acid, dihydrocaffeic acid, hydroferulic acid, hydroisoferulic acid, umbellic acid, caffeic acid (coffee acid), ferulic acid, isoferulic acid, sinapic acid, syringic acid, dehydroquinic acid, dehydroshikimic acid, shikimic acid, chorismic acid, L-tryptophan, L-tyrosine, prephenic acid, arogenic acid, and L-phenylalanine.

Furthermore, other specific examples of the cyclic compound include flavonoid, lignan, chalcone, stilbenoid, alkaloid, curcuminoid, terpenoid, saponin, various glucosides, polyphenols such as various polyphenol-based aromatic compounds, amino acids, and vitamins.

Among these, examples of flavonoid include anthocyanidins such as aurantinidin, cyanidin, delphinidin, europinidin, luteolinidin, pelargonidin, malvidin, peonidin, petunidin, and rosinidin; anthocyanins such as procyanidin; flavanones such as naringenin, eriocitrin, pinocembrin, and eriodictyol; flavans such as catechin; flavones such as apigenin, luteolin, baicalein, and chrysin; flavonols such as quercetin and kempferol; isoflavonoids such as isoflavon, isoflavane, isoflavanediol, and genistein; neoflavonoid, biflavonoid, aurone, prenylflavonoid, and O-methylated flavonoid.

Examples of lignans include pinoresinol, lariciresinol, secoisolariciresinol, matairesinol, hydroxymatairesinol, syringaresinol, sesamin, arctigenin, sesaminol, podophyllotoxin, and steganacin.

Examples of stilbenoid include aglycone such as piceatannol, pinosylvin, pterostilbene, resveratrol, 4'-methoxyresveratrol, pinostilbene, and pisiatanol; and oligomers such as α-viniferin, ampelopsis A, ampelopsin E, diptoindonesin C-Kawan, diptoindonesin F-Damarbua, ε-viniferin, flexosol A, gnetin H, hemsleyanol D, hopeaphenol, diptoindonesin B, and vaticanol B.

Examples of curcuminoid include curcumin and shogaol.

Examples of terpenoid include carotenoids such as lutein, vitamin A, vitamin E, and β-carotene; and steroids such as sitosterol.

Examples of various glucosides include phenol glucosides such as salicin, β-glucogallin, salicylic acid glucoside, salidroside, gastrodin, populin, phlorizin, and arbutin; coumarin glucosides such as esculin; flavonoid glucosides such as hesperidin and rutin; and stilbenoid glucosides such as astringin, piceid, and diptoindonesin A.

Examples of various polyphenol-based aromatic compounds include tyrosol, hydroxytyrosol, esculetin, phloretin, rosmarinic acid, salvianic acid A, reticulin, paracoumaryl alcohol, coniferyl alcohol, and caffeyl alcohol.

Examples of amino acids include phenylalanine and tyrosine.

Examples of vitamins include vitamin A, vitamin D, and vitamin E.

Furthermore, other specific examples of the cyclic compound include an aromatic compound, an alicyclic compound, an aliphatic compound, and a heterocyclic compound.

Among these, examples of the aromatic compound include vanillin, 2-phenylethanol, phenylacetic acid, cinnamic alcohol, isoeugenol, ferulic acid, 4-aminobenzoic acid, anethole, estragole, methyl anthranilate, methyl cinnamate, ethyl cinnamate, phenylacetaldehyde, cinnamic aldehyde, cinnamyl acetate, resorcin, 4-vinylphenol, 4-vinyl-2-methoxyphenol, 3,4-dihydroxystyrene, dopamine, levodopa, hydroquinone, coumarin, 7-hydroxycoumarin, 4-hydroxycoumarin, and xiamenmycin A.

Examples of the alicyclic compound include carveol, perillyl alcohol, borneol, methyl jasmonate, 1,8-cineol, L-menthone, valencene, nootkatone, α-pinene, camphene, L-carvone, perillyl aldehyde, myrtenal, L-menthyl acetate, and β-ionone.

Examples of the aliphatic compound include cis-3-hexenol, cis-3-hexenyl acetate, acetoin, nerol, farnesol, arginine, and muconic acid.

Examples of the heterocyclic compound include niacin, niacinamide, maltol, and indole.

On the other hand, regarding the derivative of the cyclic compound, for example, an ester, an acid anhydride, an amide, an acid halide, a salt, and the like of the above-mentioned compound; or all compounds derived from the cyclic compound may be mentioned.

Among the cyclic compounds such as described above, the cyclic compound represented by General Formula (1) is more preferably at least one selected from the group consisting of 2-hydroxybenzoic acid, 3-hydroxybenzoic acid, 4-hydroxybenzoic acid, 2,3-dihydroxybenzoic acid, 2,4-dihydroxybenzoic acid, 2,5-dihydroxybenzoic acid, 2,6-dihydroxybenzoic acid, 3,4-dihydroxybenzoic acid, and 3,5-dihydroxybenzoic acid. By using these, a flavor that has various efficacies and is safer can be realized.

The molecular weight of the cyclic compound or the derivative thereof is not limited; however, the molecular weight is preferably 120 to 1000, and more preferably 130 to 800.

Furthermore, in a case where ring A of the cyclic compound represented by General Formula (1) is a 5-membered ring of a saturated ring or a partially saturated ring, in which all the ring-constituting atoms are carbon atoms, it is preferable that one or more of the carbon atoms of ring A to which $R^2$ to $R^5$ and X are bonded are asymmetric carbon atoms. In a case where ring A of the cyclic compound represented by General Formula (1) is a 6-membered ring of a saturated ring or a partially saturated ring, in which all the ring-constituting atoms are carbon atoms, it is preferable that one or more of the carbon atoms of ring A to which $R^2$ to $R^6$ and X are bonded are asymmetric carbon atoms.

In such a case, the cyclic compound is a stereoisomer, and thereby a meaningful flavor can be realized. Furthermore, by producing such a cyclic compound from a plant-derived saccharide, a flavor including a specific stereoisomer with high purity can be obtained. That is, a flavor including a specific stereoisomer with high purity and having a low content percentage of other stereoisomers can be obtained. Such a flavor is useful from the viewpoint that a flavor having excellent safety and efficacy can be realized. Furthermore, since a complicated production step for removing unnecessary stereoisomers is not required, reduction of the production cost can be attempted.

Furthermore, when the carbon atom of ring A to which X is bonded in the cyclic compound represented by General Formula (1) is denoted by $C^1$; the carbon atom of ring A to which $R^2$ is bonded is denoted by $C^2$; the carbon atom of ring A to which $R^3$ is bonded is denoted by $C^3$; the carbon atom of ring A to which $R^4$ is bonded is denoted by $C^4$; the carbon atom of ring A to which $R^5$ is bonded is denoted by $C^5$; and the carbon atom of ring A to which $R^6$ is bonded is denoted by $C^6$, it is preferable that the combination in which these carbon atoms are asymmetric carbon atoms is any one selected from the group consisting of the following (a) to (h):

(a) $C^1$ (b) $C^2$ (c) $C^3$ (d) $C^4$ (e) $C^1$ and $C^4$ (f) $C^3$ and $C^4$ (g) $C^1$, $C^3$, and $C^4$ (h) $C^3$, $C^4$, and $C^5$ The General Formula (2) described in the fourth embodiment is a formula in which the indications of $C^1$ to $C^6$ have been added to the cyclic compound represented by General Formula (1).

In such a case, the cyclic compound is a stereoisomer, and thereby a more meaningful flavor can be realized. By producing such a cyclic compound from a plant-derived saccharide, a flavor including a specific stereoisomer with high purity, which is one selected from the group consisting of the above-described (a) to (h), can be obtained. That is, a flavor including a specific stereoisomer with high purity and having a low content percentage of other stereoisomers can be obtained. Such a flavor is useful from the viewpoint that a flavor having excellent safety and efficacy can be realized. Furthermore, since any complicated production steps associated with the removal of unnecessary stereoisomers can be cut down, the production cost can be reduced.

The cyclic compound and a derivative thereof according to the present embodiment are compounds represented by the above-described General Formula (2), and in addition, it is preferable that the cyclic compound is 3-dehydroquinate, 3-dehydroshikimic acid, shikimic acid, chorismic acid, or prephenic acid. All of these compounds can be produced from plant-derived saccharides and are useful as flavors. Therefore, by using these compounds produced from plant-derived saccharides, a flavor that has superior efficacy and is safer can be realized.

The structures of these cyclic compounds are represented by the following formulae.

3-Dehydroquinate

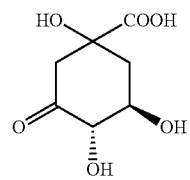 [SMILES: O=C1CC(O)(C(=O)O)C[C@@H](O)[C@@H]1O]

3-Dehydroshikimic Acid

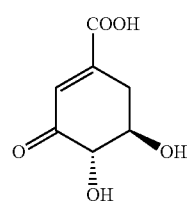 [SMILES: O=C(O)C1=CC(=O)[C@@H](O)[C@H](O)C1]

Shikimic Acid

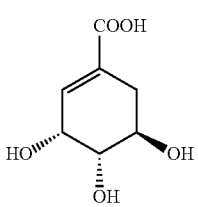 [SMILES: O=C(O)C1=C[C@@H](O)[C@@H](O)[C@H](O)C1]

Chorismic Acid

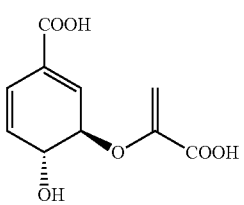 [SMILES: C=C(O[C@@H]1C=C(C(=O)O)C=C[C@H]1O)C(=O)O]

Prephenic Acid

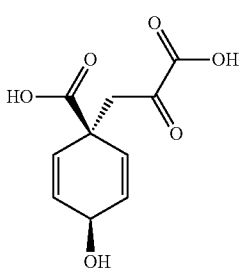 [SMILES: O=C(O)C(=O)C[C@]1(C(=O)O)C=C[C@@H](O)C=C1]

Examples of the flavor containing at least one of the cyclic compound such as described above and a derivative thereof include food flavors (flavors) and cosmetic fragrances (fragrances). Among these, regarding the function of food flavors, for example, flavoring, perfuming, flavor correction, sweetness enhancement, acidity and bitterness reduction, and promotion of appetite enhancement may be mentioned.

Examples of the cosmetic fragrances include perfumes, colognes, toiletry products, household products, and air fresheners.

Examples of the form of the flavor include a water-soluble liquid, an oil-soluble liquid, an emulsified body (emulsion), and a powder.

<<Method for Producing Cyclic Compound or Derivative Thereof>>

The above-mentioned cyclic compound or a derivative thereof is produced by a bioprocess that uses a microorganism, by using a plant-derived saccharide as a raw material. That is, the above-mentioned cyclic compound or a derivative thereof is derived from a plant-derived saccharide and a microorganism.

Regarding specific examples and production methods of the materials from which the cyclic compound or a derivative thereof is derived, raw materials, materials to be used, and the like, for example, the method described in the fourth embodiment can be adopted. More specifically, according to the fourth embodiment, preparing a culture liquid, concentration, and an isolation and purification can be carried out.

<Processing into Flavor>

A flavor is obtained by processing, as necessary, the cyclic compound produced as described above or a derivative thereof. An example of such processing may be addition of optional components. The flavor of the present embodiment may include any other component to the extent that the effect of the present embodiment is not impaired.

Examples of the other components include sugar, condensed milk, wheat flour, shortening, table salt, glucose, chicken egg, butter, margarine, starch syrup, calcium, iron, seasonings, spices, oils (animal and vegetable oils, mineral oils, ester oils, wax oils, silicone oils, higher alcohols, phospholipids, fatty acids, and the like), surfactants (anionic, cationic, amphoteric, or nonionic surfactants), vitamins (vitamin A group, vitamin B group, folic acids, nicotinic acids, pantothenic acids, biotins, vitamin C group, vitamin D group, vitamin E group, other ferulic acid, γ-oryzanol, and the like), ultraviolet absorbers (p-aminobenzoic acid, anthranilic acid, salicylic acid, salicylic acid glucoside, benzotriazole, tetrazole, imidazoline, pyrimidine, dioxane, furan, pyrone, camphor, nucleic acid, allantoin or derivatives thereof, amino acid-based compounds, shikonin, baicalin, baicalein, berberine, and the like), antioxidants (stearic acid esters, nordihydroguaiaretic acid, dibutylhydroxytoluene, butylhydroxyanisole, parahydroxyanisole, propyl gallate, sesamol, sesamolin, gossypol, and the like), thickeners (hydroxyethyl cellulose, ethyl cellulose, carboxyethyl cellulose, methyl cellulose, carboxymethyl cellulose, sodium carboxymethyl cellulose, hydoxypropyl cellulose, nitrocellulose, polyvinyl alcohol, polyvinyl methyl ether, polyvinylpyrrolidone, polyvinyl methacrylate, polyacrylic acid salts, carboxyvinyl polymers, gum arabic, tragacanth gum, agar, casein, dextrin, gelatin, pectin, starch, alginic acid or salts thereof, and the like), moisturizers (propylene glycol, 1,3-butylene glycol, polyethylene glycol, glycerin, 1,2-pentanediol, hexylene glycol, octylene glycol, chondroitin sulfate or salts thereof, hyaluronic acid or salts thereof, sodium lactate, and the like), lower alcohols, polyhydric alcohols, water-soluble polymers, pH adjusting agents, antiseptic/antifungal agents, colorants, flavors, refreshing agents, stabilizers, animal/plant extracts, animal/plant proteins or degradation products thereof, animal/plant polysaccharides or degradation products thereof, animal/plant glycoproteins or degradation products thereof, microbial culture metabolic components, blood flow promoters, anti-phlogistic agents, anti-inflammatory agents, anti-allergic agents, cell activators, amino acids or salts thereof, keratolytic agents, astringent agents, wound healing agents, foam increasing agents, oral agents, deodorizers/deodorants, and emulsifiers. These can be used singly or in combination of two or more kinds thereof.

Thus, the flavor of the present embodiment has been described above; however, specific examples of the flavor are not limited to those described above and may be any flavor.

Thus, the embodiments of the present invention have been described above; however, these are only examples of the present invention, and various configurations other than the above-described ones can be adopted.

EXAMPLES

Example I

Examples I-1 to I-4 and Comparative Examples I-1 to I-4

In the present examples, the antibacterial characteristics of a composition were evaluated.

Components were blended according to the blends described in Tables 1 to 4, and a water-soluble additive composition, specifically an antibacterial agent composition, of each example was obtained. That is, in each Example, an antibacterial agent composition was obtained by mixing 98% by mass of protocatechuic acid (reagent, manufactured by Tokyo Chemical Industry Co., Ltd.) and 2% by mass of gallic acid. On the other hand, in each Comparative Example, the protocatechuic acid was used as it was.

In each Example, aqueous solutions (antibacterial agent composition-mixed liquids) having concentrations of the antibacterial agent composition of 0.1% by mass, 0.2% by mass, 0.3% by mass, and 0.5% by mass were obtained by using the obtained composition.

The antibacterial characteristics of the obtained composition were evaluated by the following method.

(Evaluation Method)

In each example, the test solution adjusted to each concentration described above and test bacterial cells were mixed with a bacterial medium containing 1% polyoxyethylene polyoxypropylene alkyl ether. After stirring, the absorbance at 650 nm was measured, and this was denoted by the initial value. The cells were cultured under aerobic conditions at 37° C. for 24 hours, the absorbance at 650 nm was measured again, and the initial value was subtracted from this to determine the bacterial cell-derived turbidity. The test results are presented as a percentage (%) relative to an absorbance of 0% of the test sample taken as 100. As the test bacterial cells, *Staphylococcus aureus* (Example I-1 and Comparative Example I-1), *Escherichia coli* (Example I-2 and Comparative Example I-2), *Pseudomonas aeruginosa* (Example I-3 and Comparative Example I-3), and *Candida albicans* (yeast, Example I-4 and Comparative Example I-4) were used.

Figure 2:
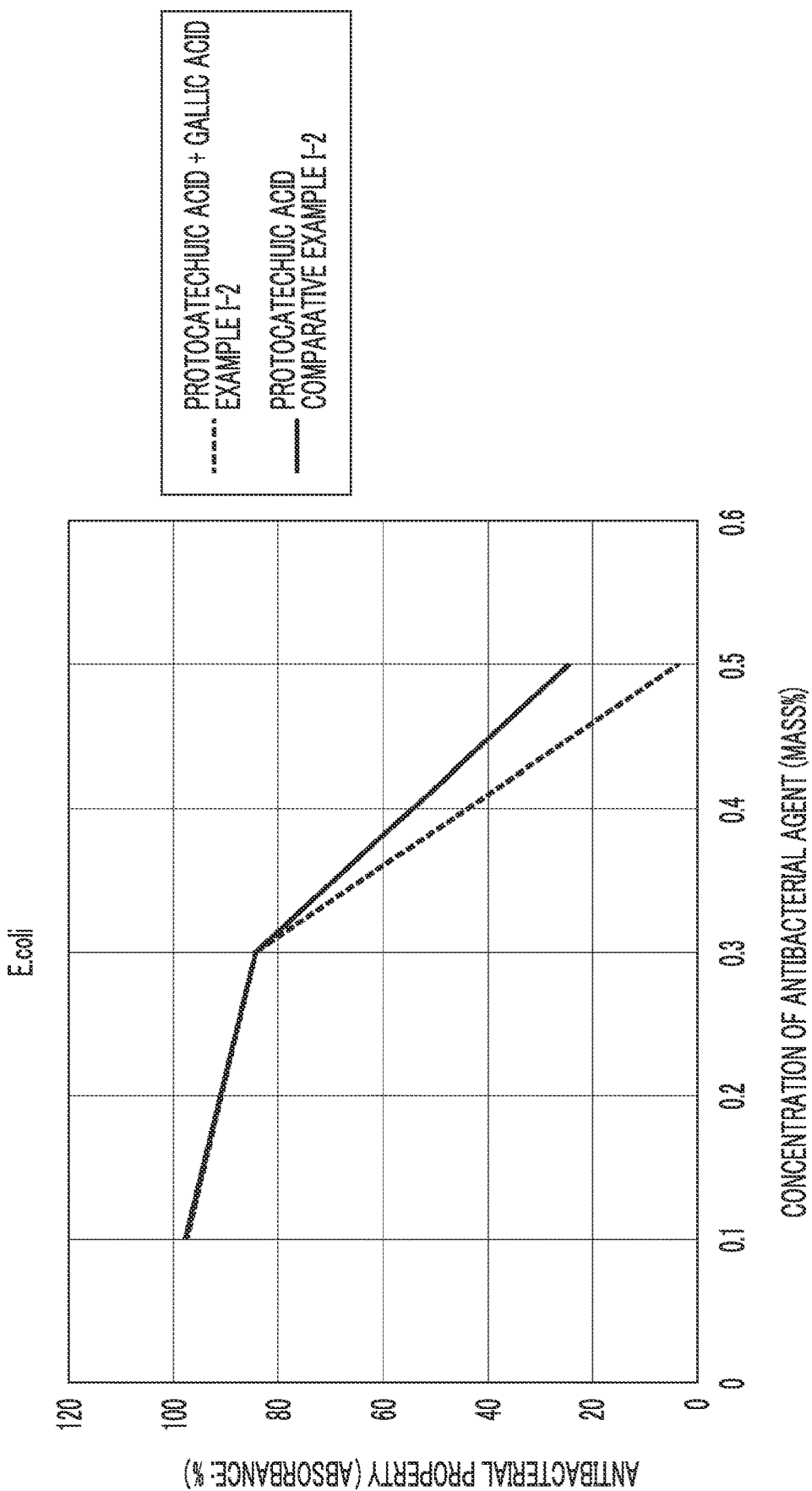
FIG. 2 is a diagram showing evaluation results for an antibacterial agent composition.
Figure 3:
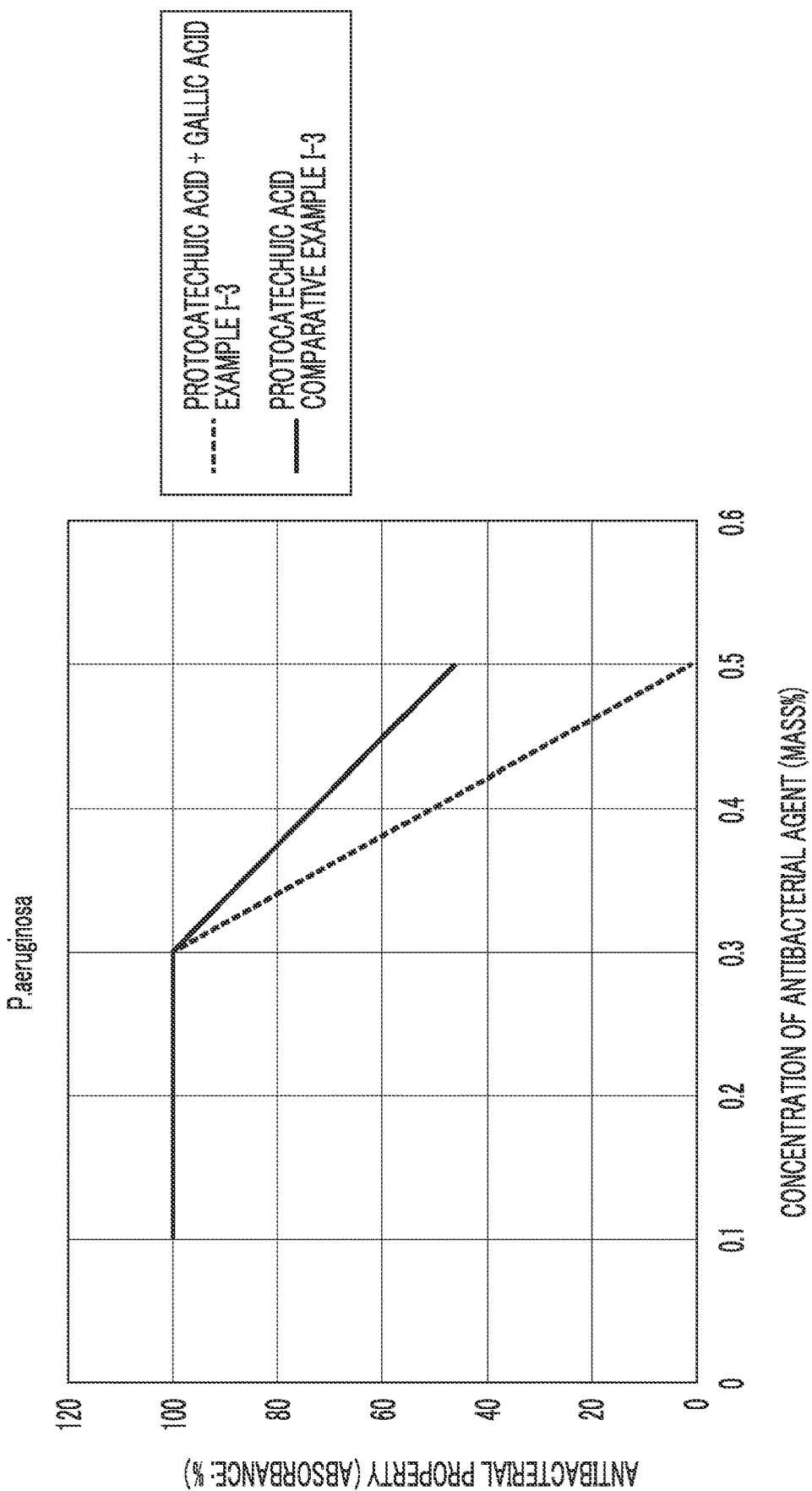
FIG. 3 is a diagram showing evaluation results for an antibacterial agent composition.
Figure 4:
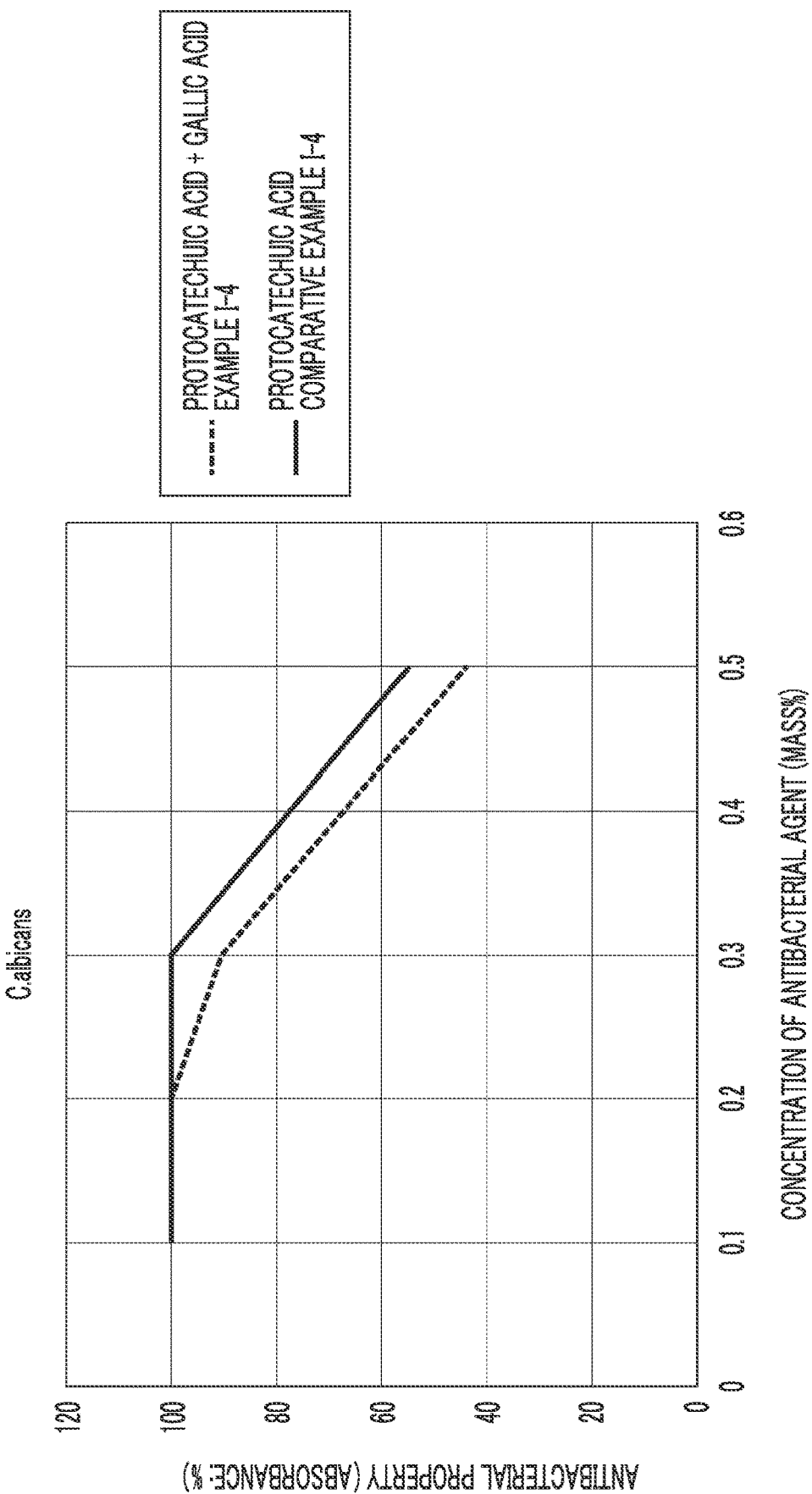
FIG. 4 is a diagram showing evaluation results for an antibacterial agent composition.

The evaluation results are shown together in Table 1 to Table 4 and are also shown in FIG. 1 to FIG. 4. FIG. 1 to FIG. 4 are diagrams showing the evaluation results for the antibacterial agent compositions.

TABLE 1

| | Example I-1 | | | | Comparative Example I-1 | | | |
|---|---|---|---|---|---|---|---|---|
| Composition of antibacterial agent | Protocatechuic acid 98% Gallic acid 2% | Protocatechuic acid 98% Gallic acid 2% | Protocatechuic acid 98% Gallic acid 2% | Protocatechuic acid 98% Gallic acid 2% | Protocatechuic acid 100% | Protocatechuic acid 100% | Protocatechuic acid 100% | Protocatechuic acid 100% |
| Solvent | Water | Water | Water | Water | Water | Water | Water | Water |
| Concentration of antibacterial agent (mass %) | 0.1 | 0.2 | 0.3 | 0.5 | 0.1 | 0.2 | 0.3 | 0.5 |
| Type of bacterium | *S. aureus* | | | | | | | |
| Antibacterial property (absorbance) | 58.1 | 45.9 | 33.6 | 0 | 60.1 | 52.5 | 45 | 0 |

TABLE 2

| | Example I-2 | | | | Comparative Example I-2 | | | |
|---|---|---|---|---|---|---|---|---|
| Composition of antibacterial agent | Protocatechuic acid 98% Gallic acid 2% | Protocatechuic acid 98% Gallic acid 2% | Protocatechuic acid 98% Gallic acid 2% | Protocatechuic acid 98% Gallic acid 2% | Protocatechuic acid 100% | Protocatechuic acid 100% | Protocatechuic acid 100% | Protocatechuic acid 100% |
| Solvent | Water | Water | Water | Water | Water | Water | Water | Water |
| Concentration of antibacterial agent (mass %) | 0.1 | 0.2 | 0.3 | 0.5 | 0.1 | 0.2 | 0.3 | 0.5 |
| Type of bacterium | *E. coli* | | | | | | | |
| Antibacterial property (absorbance) | 97.4 | 90.8 | 84.2 | 3.4 | 97.6 | 90.85 | 84.1 | 24.4 |

TABLE 3

| | Example I-3 | | | | Comparative Example I-3 | | | |
|---|---|---|---|---|---|---|---|---|
| Composition of antibacterial agent | Protocatechuic acid 98% Gallic acid 2% | Protocatechuic acid 98% Gallic acid 2% | Protocatechuic acid 98% Gallic acid 2% | Protocatechuic acid 98% Gallic acid 2% | Protocatechuic acid 100% | Protocatechuic acid 100% | Protocatechuic acid 100% | Protocatechuic acid 100% |
| Solvent | Water | Water | Water | Water | Water | Water | Water | Water |
| Concentration of antibacterial agent (mass %) | 0.1 | 0.2 | 0.3 | 0.5 | 0.1 | 0.2 | 0.3 | 0.5 |
| Type of bacterium | *P. aeruginosa* | | | | | | | |
| Antibacterial property (absorbance) | 100 | 100 | 100 | 0.7 | 100 | 100 | 100 | 46 |

TABLE 4

| | Example I-4 | | | | Comparative Example I-4 | | | |
|---|---|---|---|---|---|---|---|---|
| Composition of antibacterial agent | Protocatechuic acid 98% Gallic acid 2% | Protocatechuic acid 98% Gallic acid 2% | Protocatechuic acid 98% Gallic acid 2% | Protocatechuic acid 98% Gallic acid 2% | Protocatechuic acid 100% | Protocatechuic acid 100% | Protocatechuic acid 100% | Protocatechuic acid 100% |
| Solvent | Water | Water | Water | Water | Water | Water | Water | Water |
| Concentration of antibacterial agent (mass %) | 0.1 | 0.2 | 0.3 | 0.5 | 0.1 | 0.2 | 0.3 | 0.5 |
| Type of bacterium | *C. albicans* | | | | | | | |

TABLE 4-continued

|  | Example I-4 | | | | Comparative Example I-4 | | | |
|---|---|---|---|---|---|---|---|---|
| Antibacterial property (absorbance) | 100 | 100 | 90.6 | 44 | 100 | 100 | 100 | 54.8 |

From Table 1 to Table 4 and FIG. 1 to FIG. 4, the composition obtained in each of the Examples tended to have a lower absorbance as compared to those of the Comparative Examples, and the composition exhibited excellent antibacterial characteristics.

Examples I-5 to I-7 and Comparative Examples I-5 to I-7

Components were blended according to the blends described in Table 5 to Table 7, and water-soluble additive compositions including a cyclic carboxylic acid were obtained according to Example I-1 or Comparative Example I-1.

Here, in Example I-5 and Comparative Example I-5, shikimic acid (reagent, manufactured by Fujifilm Wako Pure Chemical Corporation) was used. In Example I-6 and Comparative Example I-6, 4-hydroxybenzoic acid (reagent, manufactured by Fujifilm Wako Pure Chemical Corporation) was used. In Example I-7 and Comparative Example I-7, 4-aminobenzoic acid (reagent, manufactured by Fujifilm Wako Pure Chemical Corporation) was used.

In each Example, aqueous solutions (antibacterial agent composition-mixed liquids) having concentrations of the antibacterial agent composition of 0.1% by mass, 0.2% by mass, 0.3% by mass, and 0.5% by mass were obtained by using the obtained composition.

For the obtained compositions, the antibacterial characteristics were evaluated according to Example I-1 or Comparative Example I-1 using *Staphylococcus aureus* as the test bacterial cells. The evaluation results are shown together in Table 5 to Table 7.

TABLE 5

|  | Example I-5 | | | | Comparative Example I-5 | | | |
|---|---|---|---|---|---|---|---|---|
| Composition of antibacterial agent | Shikimic acid 98% Gallic acid 2% | Shikimic acid 98% Gallic acid 2% | Shikimic acid 98% Gallic acid 2% | Shikimic acid 98% Gallic acid 2% | Shikimic acid 100% | Shikimic acid 100% | Shikimic acid 100% | Shikimic acid 100% |
| Solvent | Water | Water | Water | Water | Water | Water | Water | Water |
| Concentration of antibacterial agent (mass %) | 0.1 | 0.2 | 0.3 | 0.5 | 0.1 | 0.2 | 0.3 | 0.5 |
| Type of bacterium | | | | *S. aureus* | | | | |
| Antibacterial property (absorbance) | 80 | 70 | 52 | 18 | 87 | 80 | 70 | 26 |

TABLE 6

|  | Example I-6 | | | | Comparative Example I-6 | | | |
|---|---|---|---|---|---|---|---|---|
| Composition of antibacterial agent | 4-Hydroxybenzoic acid 98% Gallic acid 2% | 4-Hydroxybenzoic acid 98% Gallic acid 2% | 4-Hydroxybenzoic acid 98% Gallic acid 2% | 4-Hydroxybenzoic acid 98% Gallic acid 2% | 4-Hydroxybenzoic acid 100% | 4-Hydroxybenzoic acid 100% | 4-Hydroxybenzoic acid 100% | 4-Hydroxybenzoic acid 100% |
| Solvent | Water | Water | Water | Water | Water | Water | Water | Water |
| Concentration of antibacterial agent (mass %) | 0.1 | 0.2 | 0.3 | 0.5 | 0.1 | 0.2 | 0.3 | 0.5 |
| Type of bacterium | | | | *S. aureus* | | | | |
| Antibacterial property (absorbance) | 47 | 31 | 20 | 0 | 53 | 41 | 28 | 0 |

TABLE 7

|  | Example I-7 | | | | Comparative Example I-7 | | | |
|---|---|---|---|---|---|---|---|---|
| Composition of antibacterial agent | 4-Aminobenzoic acid 98% Gallic acid 2% | 4-Aminobenzoic acid 98% Gallic acid 2% | 4-Aminobenzoic acid 98% Gallic acid 2% | 4-Aminobenzoic acid 98% Gallic acid 2% | 4-Aminobenzoic acid 100% | 4-Aminobenzoic acid 100% | 4-Aminobenzoic acid 100% | 4-Aminobenzoic acid 100% |

TABLE 7-continued

| | Example I-7 | | | | Comparative Example I-7 | | | |
|---|---|---|---|---|---|---|---|---|
| Solvent | Water | Water | Water | Water | Water | Water | Water | Water |
| Concentration of antibacterial agent (mass %) | 0.1 | 0.2 | 0.3 | 0.5 | 0.1 | 0.2 | 0.3 | 0.5 |
| Type of bacterium | | | | *S. aureus* | | | | |
| Antibacterial property (absorbance) | 45 | 34 | 23 | 0 | 56 | 45 | 32 | 0 |

Example II

Examples II-1 to II-4 and Comparative Examples II-1 and II-2

In the present examples, water-soluble additive compositions were prepared, their solubility characteristics were evaluated, and in addition, the purity of the cyclic carboxylic acid in the composition was evaluated.

Example II-1

<Production of Protocatechuic Acid by Bioprocess>

Protocatechuic acid was produced by a bioprocess in a 10-L jar fermenter. Regarding the medium, an LB medium in which saccharide purified from sugar cane pomace was dissolved at a proportion of 10% was used.
<Collection of Protocatechuic Acid Composition from Culture Liquid Through Concentration and Purification Process>

A culture liquid obtained by the bioprocess was subjected to a concentration treatment by reduced pressure concentration so that the total solid content concentration would be 15% to 30% by mass. The degree of pressure reduction was set to 100 to 5000 Pa, the liquid temperature was set to 30° C. to 80° C., and the concentration treatment was carried out using a reduced pressure distillation facility. Although the degree of concentration depends on the treatment time, a concentrated liquid having a total solid content concentration of 15% to 30% by mass was collected by the concentration treatment for 6 to 8 hours. Hydrochloric acid was added to this concentrated liquid to adjust the pH to be equal to or less than 4, and the mixture was further cooled to 0° C. to room temperature. A crystallization product was collected by filtration, washed three times with pure water in an amount 20 times the mass of the precipitate, and then dried under reduced pressure, and a powdery water-soluble additive composition including protocatechuic acid was collected.

Example II-2

A composition including protocatechuic acid was collected according to Example II-1, except that after the culture liquid was concentrated, washing with pure water in an amount 20 times the mass of the filtered precipitate was performed four times.

Example II-3

A composition including protocatechuic acid was collected according to Example II-1, except that after the culture liquid was concentrated, washing with pure water in an amount 20 times the mass of the filtered precipitate was performed two times.

Example II-4

A composition including protocatechuic acid was collected according to Example II-1, except that after the culture liquid was concentrated, washing with pure water in an amount 20 times the mass of the filtered precipitate was performed one time.

Comparative Example II-1

A commercially available reagent of protocatechuic acid (manufactured by Tokyo Chemical Industry Co., Ltd.) was prepared.

Comparative Example II-2

A composition including protocatechuic acid was collected according to Example II-1, except that after the culture liquid was concentrated, washing of the filtered precipitate was not performed.
(Evaluation Method)
(Cyclic Carboxylic Acid Concentration)

For the composition obtained in each example, the concentration of the cyclic carboxylic acid was measured by high performance liquid chromatography (HPLC). The measurement conditions are as follows.

Column: COSMOSIL 5C18-AR-II (0.6 mm×250 mm) manufactured by Nacalai Tesque, Inc.

Mobile phase: Water/methanol/perchloric acid=4/1/0.0075 (vol/vol/vol) isocratic elution Flow rate: 1 mL/mmin Column temperature: 40° C.

Detection method: Photodiode array (PDA) detector (210 nm)
(Ion Concentration)

For the composition obtained in each example, the respective ion concentrations of $Na^+$, $NH_4^+$, $K^+$, $SO_4^{2-}$, $PO_4^{3-}$, $NO_2^-$, $NO_3^-$, and $Cl^-$ and the total inorganic ion concentration (ppm, excluding hydrogen ions and hydroxyl group ions) were measured by ion chromatography. The measurement conditions are as follows.

Column: (Cation) Shim-pack IC-C4 (manufactured by Shimadzu Corporation), (Anion) Shim-pack IC-SA2 (manufactured by Shimadzu Corporation)

Mobile phase: (Cation) water/oxalic acid dihydrate=1000/0.315 (mass/mass), (anion) water/sodium hydrogen carbonate/sodium carbonate=1000/1.008/0.0636 (mass/mass/mass), isocratic elution for both anions and cations Flow rate: 1 mL/mmin (for both cations and anions)

Column temperature: (cation) 40° C., (anion) 30° C.
Detection method: Electrical conductivity detector The concentration of each ion was calculated as a proportion (ppm) of the concentration (ppm) of each ion with respect to the concentration (ppm) of the cyclic carboxylic acid in the composition as measured by HPLC. The measurement results are shown in Table 8.

(Purity)

Among the measurement results for the above-mentioned ion concentration, the purity of the cyclic carboxylic acid in the composition was determined according to the following criteria based on the total inorganic ion concentration (excluding hydrogen ions and hydroxyl group ions), and results with the following ratings "⊚" and "○" were considered acceptable. The results are shown in Table 8.

⊚: The total amount of inorganic ions is equal to or more than 0 and less than 1000.

○: The total amount of inorganic ions is equal to or more than 1000 and less than 5000.

x: The total amount of inorganic ions is equal to or more than 5000 ppm.

(Solubility)

For the composition obtained in each example, 50 g of the composition was added to 1 L of pure water whose liquid temperature was adjusted to 25° C., and the mixture was stirred with a stirrer for one day, and then the cyclic carboxylic acid concentration in the supernatant was measured by HPLC to calculate the solubility. Compositions having a solubility of equal to or more than 12 g/L were considered acceptable. The measurement results are shown in Table 8.

TABLE 8

| | Example II-1 | Example II-2 | Example II-3 | Example II-4 | Comparative Example II-1 | Comparative Example II-2 |
|---|---|---|---|---|---|---|
| $NH_4^+$ [ppm] | 317 | 209 | 452 | 1128 | 4 | 2476 |
| $Na^+$ [ppm] | 170 | 21 | 500 | 2491 | 3 | 3479 |
| $K^+$ [ppm] | 36 | 75 | 48 | 95 | 32 | 103 |
| $SO_4^{2-}$ [ppm] | 44 | 21 | 67 | 721 | 89 | 1082 |
| $PO_4^{3-}$ [ppm] | 160 | 0 | 175 | 201 | 0 | 503 |
| $NO_2^-$ [ppm] | 7 | 6 | 5 | 3 | 23 | 9 |
| $NO_3^-$ [ppm] | 23 | 0 | 31 | 24 | 105 | 69 |
| $Cl^-$ [ppm] | 27 | 10 | 40 | 35 | 33 | 28 |
| Total inorganic ions [ppm] | 784 | 342 | 1318 | 4698 | 289 | 7749 |
| Solubility of PCA @25° C. [g/L] | 13 | 12 | 13 | 15 | 11 | 16 |
| Purity of PCA | ⊚ | ⊚ | ○ | ○ | ⊚ | X |

From Table 8, the composition obtained in each Example had high purity of protocatechuic acid and excellent water solubility of protocatechuic acid.

Examples II-5 to II-8 and Comparative Examples II-3 and II-4

A water-soluble additive composition including shikimic acid instead of protocatechuic acid was prepared, the solubility characteristics of the composition were evaluated, and the purity of the cyclic carboxylic acid in the composition was evaluated.

Example II-5

<Production of Shikimic Acid by Bioprocess>

Shikimic acid was produced by a bioprocess in a 10-L jar fermenter. Regarding the medium, an LB medium in which saccharide purified from sugar cane pomace was dissolved at a proportion of 10% was used.

<Collection of Shikimic Acid Composition from Culture Liquid Through Concentration and Purification Process>

A culture liquid obtained by the bioprocess was subjected to a concentration treatment by reduced pressure concentration so that the total solid content concentration would be 15% to 30% by mass. The degree of pressure reduction was set to 100 to 5000 Pa, the liquid temperature was set to 30° C. to 80° C., and the concentration treatment was carried out using a reduced pressure distillation facility. Although the degree of concentration depends on the treatment time, a concentrated liquid having a total solid content concentration of 15% to 30% by mass was collected by the concentration treatment for 6 to 8 hours. Hydrochloric acid was added to this concentrated liquid to adjust the pH to be equal to or less than 4, and the mixture was further cooled to 0° C. to room temperature. A crystallization product was collected by filtration, washed three times with pure water in an amount 20 times the mass of the precipitate, and then dried under reduced pressure, and a powdery water-soluble additive composition including shikimic acid was collected.

Example II-6

A composition including shikimic acid was collected according to Example II-5, except that after the culture liquid was concentrated, washing with pure water in an amount 20 times the mass of the filtered precipitate was performed four times.

Example II-7

A composition including shikimic acid was collected according to Example II-5, except that after the culture liquid was concentrated, washing with pure water in an amount 20 times the mass of the filtered precipitate was performed two times.

Example II-8

A composition including shikimic acid was collected according to Example II-5, except that after the culture liquid was concentrated, washing with pure water in an amount 20 times the mass of the filtered precipitate was performed one time.

Comparative Example II-3

A commercially available reagent of shikimic acid (manufactured by Fujifilm Wako Pure Chemical Corporation) was prepared.

Comparative Example II-4

A composition including shikimic acid was collected according to Example II-5, except that after the culture liquid was concentrated, washing of the filtered precipitate was not performed.

(Evaluation Method)

For the composition obtained in each example, the cyclic carboxylic acid concentration, the ion concentration, the purity, and the solubility were evaluated according to Examples II-1 to II-4 and Comparative Examples II-1 and II-2 as described above. The results are shown in Table 9.

TABLE 9

| | Example II-5 | Example II-6 | Example II-7 | Example II-8 | Comparative Example II-3 | Comparative Example II-4 |
|---|---|---|---|---|---|---|
| $NH_4^+$ [ppm] | 107 | 74 | 540 | 1184 | 8 | 2712 |
| $Na^+$ [ppm] | 189 | 117 | 436 | 2305 | 12 | 3217 |
| $K^+$ [ppm] | 28 | 52 | 58 | 92 | 0 | 104 |
| $SO_4^{2-}$ [ppm] | 31 | 19 | 69 | 840 | 18 | 932 |
| $PO_4^{3-}$ [ppm] | 45 | 0 | 99 | 265 | 31 | 376 |
| $NO_2^-$ [ppm] | 27 | 8 | 32 | 38 | 8 | 31 |
| $NO_3^-$ [Plim] | 41 | 12 | 67 | 93 | 26 | 88 |
| $Cl^-$ [ppm] | 29 | 18 | 53 | 65 | 34 | 62 |
| Total inorganic ions [ppm] | 497 | 300 | 1354 | 4882 | 137 | 7522 |
| Solubility of shikimic acid @25° C. [g/L] | 195 | 192 | 198 | 199 | 179 | 201 |
| Purity of shikimic acid | ◎ | ◎ | ○ | ○ | ◎ | X |

Examples II-9 to II-12 and Comparative Examples II-5 and II-6

A water-soluble additive composition including 4-hydroxybenzoic acid instead of protocatechuic acid was prepared, the solubility characteristics of the composition were evaluated, and the purity of the cyclic carboxylic acid in the composition was evaluated.

Example II-9

<Production of 4-Hydroxybenzoic Acid by Bioprocess>

4-Hydroxybenzoic acid was produced by a bioprocess in a 10-L jar fermenter. Regarding the medium, an LB medium in which saccharide purified from sugar cane pomace was dissolved at a proportion of 10% was used.

<Collection of 4-Hydroxybenzoic Acid Composition from Culture Liquid Through Concentration and Purification Process>

A culture liquid obtained by the bioprocess was subjected to a concentration treatment by reduced pressure concentration so that the total solid content concentration would be 15% to 30% by mass. The degree of pressure reduction was set to 100 to 5000 Pa, the liquid temperature was set to 30° C. to 80° C., and the concentration treatment was carried out using a reduced pressure distillation facility. Although the degree of concentration depends on the treatment time, a concentrated liquid having a total solid content concentration of 15% to 30% by mass was collected by the concentration treatment for 6 to 8 hours. Hydrochloric acid was added to this concentrated liquid to adjust the pH to be equal to or less than 4, and the mixture was further cooled to 0° C. to room temperature. A crystallization product was collected by filtration, washed three times with pure water in an amount 20 times the mass of the precipitate, and then dried under reduced pressure, and a powdery water-soluble additive composition including 4-hydroxybenzoic acid was collected.

Example II-10

A composition including 4-hydroxybenzoic acid was collected according to Example II-9, except that after the culture liquid was concentrated, washing with pure water in an amount 20 times the mass of the filtered precipitate was performed four times.

Example II-11

A composition including 4-hydroxybenzoic acid was collected according to Example II-9, except that after the culture liquid was concentrated, washing with pure water in an amount 20 times the mass of the filtered precipitate was performed two times.

Example II-12

A composition including 4-hydroxybenzoic acid was collected according to Example II-9, except that after the culture liquid was concentrated, washing with pure water in an amount 20 times the mass of the filtered precipitate was performed one time.

Comparative Example II-5

A commercially available reagent of 4-hydroxybenzoic acid reagent (manufactured by Fujifilm Wako Pure Chemical Corporation) was prepared.

Comparative Example II-6

A composition including 4-hydroxybenzoic acid was collected according to Example II-9, except that after the culture liquid was concentrated, washing of the filtered precipitate was not performed.

(Evaluation Method)

For the composition obtained in each example, the cyclic carboxylic acid concentration, the ion concentration, the purity, and the solubility were evaluated according to Examples II-1 to II-4 and Comparative Examples II-1 and II-2 as described above. The results are shown in Table 10.

TABLE 10

|  | Example II-9 | Example II-10 | Example II-11 | Example II-12 | Comparative Example II-5 | Comparative Example II-6 |
|---|---|---|---|---|---|---|
| $NH_4^+$ [ppm] | 226 | 85 | 520 | 1216 | 5 | 2630 |
| $Na^+$ [ppm] | 153 | 132 | 479 | 2581 | 19 | 3119 |
| $K^+$ [ppm] | 30 | 42 | 55 | 89 | 28 | 95 |
| $SO_4^{2-}$ [ppm] | 38 | 17 | 74 | 693 | 54 | 950 |
| $PO_4^{3-}$ [ppm] | 36 | 3 | 109 | 270 | 31 | 357 |
| $NO_2^-$ [ppm] | 32 | 0 | 30 | 41 | 0 | 28 |
| $NO_3^-$ [ppm] | 38 | 23 | 62 | 78 | 32 | 92 |
| $Cl^-$ [ppm] | 78 | 52 | 69 | 91 | 34 | 55 |
| Total inorganic ions [ppm] | 631 | 354 | 1398 | 5059 | 203 | 7326 |
| Solubility of 4-hydroxybenzoic acid @25° C. [g/L] | 5.8 | 5.5 | 5.9 | 6.3 | 4.9 | 7.8 |
| Purity of 4-hydroxybenzoic acid | ◎ | ◎ | ○ | ○ | ◎ | X |

Examples II-13 to II-16 and Comparative Examples II-7 and II-8

A water-soluble additive composition including 4-aminobenzoic acid instead of protocatechuic acid was prepared, the solubility characteristics of the composition were evaluated, and the purity of the cyclic carboxylic acid in the composition was evaluated.

Example II-13

<Production of 4-Aminobenzoic Acid by Bioprocess>

4-Aminobenzoic acid was produced by a bioprocess in a 10-L jar fermenter. Regarding the medium, an LB medium in which saccharide purified from sugar cane pomace was dissolved at a proportion of 10% was used.

<Collection of 4-Aminobenzoic Acid Composition from Culture Liquid Through Concentration and Purification Process>

A culture liquid obtained by the bioprocess was subjected to a concentration treatment by reduced pressure concentration so that the total solid content concentration would be 15% to 30% by mass. The degree of pressure reduction was set to 100 to 5000 Pa, the liquid temperature was set to 30° C. to 80° C., and the concentration treatment was carried out using a reduced pressure distillation facility. Although the degree of concentration depends on the treatment time, a concentrated liquid having a total solid content concentration of 15% to 30% by mass was collected by the concentration treatment for 6 to 8 hours. Hydrochloric acid was added to this concentrated liquid to adjust the pH to be equal to or less than 4, and the mixture was further cooled to 0° C. to room temperature. A crystallization product was collected by filtration, washed three times with pure water in an amount 20 times the mass of the precipitate, and then dried under reduced pressure, and a powdery water-soluble additive composition including 4-aminobenzoic acid was collected.

Example II-14

A composition including 4-aminobenzoic acid was collected according to Example II-13, except that after the culture liquid was concentrated, washing with pure water in an amount 20 times the mass of the filtered precipitate was performed four times.

Example II-15

A composition including 4-aminobenzoic acid was collected according to Example II-13, except that after the culture liquid was concentrated, washing with pure water in an amount 20 times the mass of the filtered precipitate was performed two times.

Example II-16

A composition including 4-aminobenzoic acid was collected according to Example II-13, except that after the culture liquid was concentrated, washing with pure water in an amount 20 times the mass of the filtered precipitate was performed one time.

Comparative Example II-7

A commercially available reagent of 4-aminobenzoic acid (manufactured by Fujifilm Wako Pure Chemical Corporation) was prepared.

Comparative Example II-8

A composition including 4-aminobenzoic acid was collected according to Example II-13, except that after the culture liquid was concentrated, washing of the filtered precipitate was not performed.

(Evaluation Method)

For the composition obtained in each example, the cyclic carboxylic acid concentration, the ion concentration, the purity, and the solubility were evaluated according to Examples II-1 to II-4 and Comparative Examples II-1 and II-2 as described above. The results are shown in Table 11.

TABLE 11

| | Example II-13 | Example II-14 | Example II-15 | Example II-16 | Comparative Example II-7 | Comparative Example II-8 |
|---|---|---|---|---|---|---|
| $NH_4^+$ [ppm] | 223 | 85 | 640 | 1914 | 30 | 3250 |
| $Na^+$ [ppm] | 171 | 29 | 381 | 652 | 7 | 1917 |
| $K^+$ [ppm] | 43 | 31 | 61 | 79 | 2 | 95 |
| $SO_4^{2-}$ [ppm] | 29 | 13 | 37 | 61 | 21 | 109 |
| $PO_4^{3-}$ [ppm] | 51 | 29 | 55 | 92 | 15 | 113 |
| $NO_2^-$ [ppm] | 32 | 15 | 41 | 44 | 6 | 73 |
| $NO_3^-$ [ppm] | 11 | 6 | 21 | 25 | 3 | 38 |
| $Cl^-$ [ppm] | 46 | 41 | 58 | 71 | 24 | 83 |
| Total inorganic ions [ppm] | 606 | 249 | 1294 | 2938 | 108 | 5678 |
| Solubility of 4-aminobenzoic acid @25° C. [g/L] | 5.2 | 5 | 5.2 | 5.5 | 4.6 | 5.8 |
| Purity of 4-aminobenzoic acid | ◎ | ◎ | ○ | ○ | ◎ | X |

Example III

Examples III-1 to III-4 and Comparative Example III-1

In the present examples, compositions were prepared, and the moisture-retaining property and the antibacterial characteristics were evaluated. The production method and evaluation method for the composition of each example are as follows.

(Example III-1) Washing 1

<Production of Protocatechuic Acid by Bioprocess>

Protocatechuic acid was produced by a bioprocess in a 10-L jar fermenter. Regarding the medium, an LB medium in which saccharide purified from sugar cane pomace was dissolved at a proportion of 10% was used.

<Collection of Protocatechuic Acid Composition from Culture Liquid Through Concentration and Purification Process>

A culture liquid obtained by the bioprocess was subjected to a concentration treatment by reduced pressure concentration so that the total solid content concentration would be 30% to 50% by mass. The degree of pressure reduction was set to 100 to 5000 Pa, the liquid temperature was set to 30° C. to 80° C., and the concentration treatment was carried out using a reduced pressure distillation facility. Although the degree of concentration depends on the treatment time, a concentrated liquid having a total solid content concentration of 30% to 50% by mass was collected by the concentration treatment for 6 to 8 hours. Hydrochloric acid was added to this concentrated liquid to adjust the pH to be equal to or less than 4, and the mixture was further cooled to 0° C. to room temperature. A crystallization product was collected by filtration, washed once with pure water in an amount 20 times the mass of the precipitate, and then dried under reduced pressure, and a powdery water-soluble additive composition including protocatechuic acid was collected.

(Example III-2) Washing 2

A composition including protocatechuic acid was collected according to Example III-1, except that after the culture liquid was concentrated, washing with pure water in an amount 20 times the mass of the filtered precipitate was performed two times.

(Example III-3) Washing 3

A composition including protocatechuic acid was collected according to Example III-1, except that after the culture liquid was concentrated, washing with pure water in an amount 20 times the mass of the filtered precipitate was performed three times.

(Example III-4) Washing 4

A composition including protocatechuic acid was collected according to Example III-1, except that after the culture liquid was concentrated, washing with pure water in an amount 20 times the mass of the filtered precipitate was performed four times.

(Comparative Example III-1) Reagent

A commercially available reagent of protocatechuic acid (manufactured by Tokyo Chemical Industry Co., Ltd.) was prepared.

(Amino Acid Concentration)

For the composition obtained in each example, the concentration of each amino acid was measured by high performance liquid chromatography (HPLC, post-column fluorescence detection using orthophthalaldehyde as a reaction reagent, the column was Shim-pack Amino-Na manufactured by Shimadzu Corporation). The results are shown in Table 12.

(PCA Purity)

For the composition obtained in each example, the purity of the cyclic carboxylic acid in the composition was measured.

First, for the composition obtained in each example, the concentration of the cyclic carboxylic acid was measured by high performance liquid chromatography (HPLC). The measurement conditions are as follows.

Column: COSMOSIL 5C18-AR-II (0.6 mm×250 mm) manufactured by Nacalai Tesque, Inc.

Mobile phase: Water/methanol/perchloric acid=4/1/0.0075 (vol/vol/vol) isocratic elution Flow rate: 1 mL/mmin Column temperature: 40° C.

Detection method: Photodiode array (PDA) detector (210 nm)

In addition, the total inorganic ion concentration (ppm) was measured by ion chromatography. Here, the concentration of each ion was calculated as a proportion (ppm) of the concentration (ppm) of each ion with respect to the concentration (ppm) of the cyclic carboxylic acid in the composition as measured by HPLC.

Then, the purity of the cyclic carboxylic acid in the composition was determined according to the following criteria based on the measured amount of the total inorganic ion concentration. The results are shown in Table 12.

⊚: The total amount of inorganic ions is equal to or more than 0 and less than 1000.

○: The total amount of inorganic ions is equal to or more than 1000 and less than 5000.

×: The total amount of inorganic ions is equal to or more than 5000 ppm.

(Moisture-Retaining Property)

A 2.0 mass % aqueous solution of the water-soluble additive composition obtained in each example was prepared and was used as a test solution. The stratum corneum water content was measured immediately after and 15 minutes after the test solution was applied on the skin. The test results are presented as a percentage relative to a stratum corneum water content immediately after application taken as 100. The evaluation criteria are shown below. Compositions with evaluation results of "⊚" and "0" were considered acceptable.

⊚: The reduction rate of the stratum corneum water content is less than 10%.

○: The reduction rate of the stratum corneum water content is equal to or more than 10% and less than 50%.

×: The reduction rate of the stratum corneum water content is equal to or more than 50%.

The evaluation results are shown together in Table 12.

(Antibacterial Property)

A 2.0 mass % aqueous solution of the water-soluble additive composition obtained in each example was prepared and was used as a test solution.

The test solution of each example and test bacterial cells were mixed with a bacterial medium containing 1% polyoxyethylene polyoxypropylene alkyl ether. After stirring, the absorbance at 650 nm was measured, and this was denoted by the initial value. The cells were cultured under aerobic conditions at 37° C. for 24 hours, the absorbance at 650 nm was measured again, and the initial value was subtracted from this to determine the bacterial cell-derived turbidity. The test results are presented as a percentage relative to an absorbance of 0% of the test sample taken as 100. Furthermore, the following four kinds of test bacterial cells were used: *Staphylococcus aureus, Escherichia. coli, Pseudomonas aeruginosa*, and *Candida albicans* (yeast).

The evaluation criteria are shown below. Compositions with evaluation results of "⊚" and "○" were considered acceptable.

⊚: The absorbance is less than 10%.

○: The absorbance is equal to or more than 10% and less than 50%.

×: The absorbance is equal to or more than 50%.

The evaluation results are shown together in Table 12.

TABLE 12

| | Example III-1 Washing 1 | Example III-2 Washing 2 | Example III-3 Washing 3 | Example III-4 Washing 4 | Comparative Example III-1 Reagent |
|---|---|---|---|---|---|
| Aspartic Acid (ppm) | 58 | 0 | 0 | 0 | 0 |
| Glutamic Acid (ppm) | 22915 | 5040 | 1833 | 137 | 0 |
| Glycine (ppm) | 134 | 33 | 27 | 10 | 0 |
| Alanine (ppm) | 1547 | 463 | 179 | 32 | 0 |
| Valine (ppm) | 235 | 49 | 18 | 10 | 0 |
| Isoleucine (ppm) | 10 | 4 | 0 | 0 | 0 |
| Lysine (ppm) | 0 | 0 | 0 | 0 | 0 |
| Proline (ppm) | 904 | 202 | 70 | 8 | 0 |
| Total amount of amino acids (mass %) | 2.58 | 0.58 | 0.21 | 0.02 | 0.00 |
| PCA purity | ○ | ○ | ○ | ⊚ | ⊚ |
| Moisture-retaining property | ⊚ | ⊚ | ○ | ○ | × |
| Antibacterial property | ○ | ○ | ⊚ | ⊚ | ⊚ |

From Table 12, the composition obtained in each example had excellent moisture-retaining property and excellent antibacterial characteristics.

Examples III-5 to III-8 and Comparative Example III-2

In the present examples, compositions including shikimic acid instead of protocatechuic acid were prepared, and the moisture-retaining property and the antibacterial characteristics were evaluated. The production method and evaluation method for the composition of each example are as follows.

(Example III-5) Washing 1

<Production of Shikimic Acid by Bioprocess>

Shikimic acid was produced by a bioprocess in a 10-L jar fermenter. Regarding the medium, an LB medium in which saccharide purified from sugar cane pomace was dissolved at a proportion of 10% was used.

<Collection of Shikimic Acid Composition from Culture Liquid Through Concentration and Purification Process>

A culture liquid obtained by the bioprocess was subjected to a concentration treatment by reduced pressure concentration so that the total solid content concentration would be 30% to 50% by mass. The degree of pressure reduction was set to 100 to 5000 Pa, the liquid temperature was set to 30° C. to 80° C., and the concentration treatment was carried out using a reduced pressure distillation facility. Although the degree of concentration depends on the treatment time, a concentrated liquid having a total solid content concentration of 30% to 50% by mass was collected by the concentration treatment for 6 to 8 hours. Hydrochloric acid was added to this concentrated liquid to adjust the pH to be equal to or less than 4, and the mixture was further cooled to 0° C. to room temperature. A crystallization product was collected by filtration, washed once with pure water in an amount 20 times the mass of the precipitate, and then dried under reduced pressure, and a powdery water-soluble additive composition including shikimic acid was collected.

(Example III-6) Washing 2

A composition including shikimic acid was collected according to Example III-5, except that after the culture liquid was concentrated, washing with pure water in an amount 20 times the mass of the filtered precipitate was performed two times.

(Example III-7) Washing 3

A composition including shikimic acid was collected according to Example III-5, except that after the culture liquid was concentrated, washing with pure water in an amount 20 times the mass of the filtered precipitate was performed three times.

(Example III-8) Washing 4

A composition including shikimic acid was collected according to Example III-5, except that after the culture liquid was concentrated, washing with pure water in an amount 20 times the mass of the filtered precipitate was performed four times.

(Comparative Example III-2) Reagent

A commercially available reagent of shikimic acid (manufactured by Fujifilm Wako Pure Chemical Corporation) was prepared.

(Evaluation Method)

For the composition obtained in each example, the amino acid concentration, the purity, the moisture-retaining property, and the antibacterial property were evaluated according to Examples III-1 to III-4 and Comparative Example III-1 as described above. The results are shown in Table 13.

TABLE 13

|  | Example III-5 Washing 1 | Example III-6 Washing 2 | Example III-7 Washing 3 | Example III-8 Washing 4 | Comparative Example III-2 Reagent |
|---|---|---|---|---|---|
| Aspartic Acid (ppm) | 81 | 17 | 0 | 0 | 0 |
| Glutamic Acid (ppm) | 35602 | 6931 | 1942 | 201 | 0 |
| Glycine (ppm) | 165 | 31 | 25 | 6 | 0 |
| Alanine (ppm) | 2491 | 794 | 319 | 47 | 0 |
| Valine (ppm) | 362 | 85 | 37 | 21 | 0 |
| Isoleucine (ppm) | 28 | 4 | 0 | 0 | 0 |
| Lysine (ppm) | 32 | 0 | 0 | 0 | 0 |
| Proline (ppm) | 805 | 171 | 45 | 7 | 0 |
| Total amount of amino acids (mass %) | 3.96 | 0.80 | 0.24 | 0.03 | 0.00 |
| Shikimic acid purity | ○ | ○ | ○ | ◎ | ◎ |
| Moisture-retaining property | ◎ | ◎ | ○ | ○ | X |
| Antibacterial property | ○ | ○ | ◎ | ◎ | ◎ |

Examples III-9 to III-12 and Comparative Example III-3

In the present example, a composition including 4-hydroxybenzoic acid instead of protocatechuic acid was prepared, and the moisture-retaining property and the antibacterial characteristics were evaluated. The production method and evaluation method for the composition of each example are as follows.

(Example III-9) Washing 1

<Production of 4-Hydroxybenzoic Acid by Bioprocess>

4-Hydroxybenzoic acid was produced by a bioprocess in a 10-L jar fermenter. Regarding the medium, an LB medium in which saccharide purified from sugar cane pomace was dissolved at a proportion of 10% was used.

<Collection of 4-Hydroxybenzoic Acid Composition from Culture Liquid Through Concentration and Purification Process>

A culture liquid obtained by the bioprocess was subjected to a concentration treatment by reduced pressure concentration so that the total solid content concentration would be 30% to 50% by mass. The degree of pressure reduction was set to 100 to 5000 Pa, the liquid temperature was set to 30° C. to 80° C., and the concentration treatment was carried out using a reduced pressure distillation facility. Although the degree of concentration depends on the treatment time, a concentrated liquid having a total solid content concentration of 30% to 50% by mass was collected by the concentration treatment for 6 to 8 hours. Hydrochloric acid was added to this concentrated liquid to adjust the pH to be equal to or less than 4, and the mixture was further cooled to 0° C. to room temperature. A crystallization product was collected by filtration, washed once with pure water in an amount 20 times the mass of the precipitate, and then dried under reduced pressure, and a powdery water-soluble additive composition including 4-hydroxybenzoic acid was collected.

(Example III-10) Washing 2

A composition including 4-hydroxybenzoic acid was collected according to Example III-9, except that after the culture liquid was concentrated, washing with pure water in an amount 20 times the mass of the filtered precipitate was performed two times.

(Example III-11) Washing 3

A composition including 4-hydroxybenzoic acid was collected according to Example III-9, except that after the culture liquid was concentrated, washing with pure water in an amount 20 times the mass of the filtered precipitate was performed three times.

(Example III-12) Washing 4

A composition including 4-hydroxybenzoic acid was collected according to Example III-9, except that after the culture liquid was concentrated, washing with pure water in an amount 20 times the mass of the filtered precipitate was performed four times.

(Comparative Example III-3) Reagent

A commercially available reagent of 4-hydroxybenzoic acid reagent (manufactured by Fujifilm Wako Pure Chemical Corporation) was prepared.

(Evaluation Method)

For the composition obtained in each example, the amino acid concentration, the purity, the moisture-retaining property, and the antibacterial property were evaluated according to Examples III-1 to III-4 and Comparative Example III-1 as described above. The results are shown in Table 14.

TABLE 14

| | Example III-9 Washing 1 | Example III-10 Washing 2 | Example III-11 Washing 3 | Example III-12 Washing 4 | Comparative Example III-3 Reagent |
|---|---|---|---|---|---|
| Aspartic Acid (ppm) | 39 | 0 | 0 | 0 | 0 |
| Glutamic Acid (ppm) | 18076 | 3018 | 1474 | 161 | 0 |
| Glycine (ppm) | 150 | 57 | 31 | 17 | 0 |
| Alanine (ppm) | 1148 | 385 | 86 | 13 | 0 |
| Valine (ppm) | 278 | 106 | 56 | 19 | 0 |
| Isoleucine (ppm) | 0 | 0 | 0 | 0 | 0 |
| Lysine (ppm) | 18 | 5 | 0 | 0 | 0 |
| Proline (ppm) | 1015 | 251 | 59 | 3 | 0 |
| Total amount of amino acids (mass %) | 2.07 | 0.38 | 0.17 | 0.02 | 0.00 |
| 4-Hydroxybenzoic acid purity | ○ | ○ | ○ | ◎ | ◎ |
| Moisture-retaining property | ◎ | ◎ | ○ | ○ | X |
| Antibacterial property | ○ | ○ | ◎ | ◎ | ◎ |

Examples III-13 to III-16 and Comparative Example III-4

In the present examples, compositions including 4-aminobenzoic acid instead of protocatechuic acid were prepared, and the moisture-retaining property and the antibacterial characteristics were evaluated. The production method and evaluation method for the composition of each example are as follows.

(Example III-13) Washing 1

<Production of 4-Aminobenzoic Acid by Bioprocess>
4-Aminobenzoic acid was produced by a bioprocess in a 10-L jar fermenter. Regarding the medium, an LB medium in which saccharide purified from sugar cane pomace was dissolved at a proportion of 10% was used.
<Collection of 4-Aminobenzoic Acid Composition from Culture Liquid Through Concentration and Purification Process>
A culture liquid obtained by the bioprocess was subjected to a concentration treatment by reduced pressure concentration so that the total solid content concentration would be 30% to 50% by mass. The degree of pressure reduction was set to 100 to 5000 Pa, the liquid temperature was set to 30° C. to 80° C., and the concentration treatment was carried out using a reduced pressure distillation facility. Although the degree of concentration depends on the treatment time, a concentrated liquid having a total solid content concentration of 30% to 50% by mass was collected by the concentration treatment for 6 to 8 hours. Hydrochloric acid was added to this concentrated liquid to adjust the pH to be equal to or less than 4, and the mixture was further cooled to 0° C. to room temperature. A crystallization product was collected by filtration, washed one time with pure water in an amount 20 times the mass of the precipitate, and then dried under reduced pressure, and a powdery water-soluble additive composition including 4-aminobenzoic acid was collected.

(Example III-14) Washing 2

A composition including 4-aminobenzoic acid was collected according to Example III-13, except that after the culture liquid was concentrated, washing with pure water in an amount 20 times the mass of the filtered precipitate was performed two times.

(Example III-15) Washing 3

A composition including 4-aminobenzoic acid was collected according to Example III-13, except that after the culture liquid was concentrated, washing with pure water in an amount 20 times the mass of the filtered precipitate was performed three times.

(Example III-16) Washing 4

A composition including 4-aminobenzoic acid was collected according to Example III-13, except that after the culture liquid was concentrated, washing with pure water in an amount 20 times the mass of the filtered precipitate was performed four times.

(Comparative Example III-4) Reagent

A commercially available reagent of 4-aminobenzoic acid (manufactured by Fujifilm Wako Pure Chemical Corporation) was prepared.
(Evaluation Method)
For the composition obtained in each example, the amino acid concentration, the purity, the moisture-retaining property, and the antibacterial property were evaluated according to Examples III-1 to III-4 and Comparative Example III-1 as described above. The results are shown in Table 15.

TABLE 15

| | Example III-13 Washing 1 | Example III-14 Washing 2 | Example III-15 Washing 3 | Example III-16 Washing 4 | Comparative Example III-4 Reagent |
|---|---|---|---|---|---|
| Aspartic Acid (ppm) | 42 | 1 | 0 | 0 | 0 |
| Glutamic Acid (ppm) | 20741 | 2869 | 1752 | 131 | 0 |
| Glycine (ppm) | 136 | 29 | 24 | 14 | 0 |
| Alanine (ppm) | 1379 | 525 | 108 | 27 | 0 |
| Valine (ppm) | 197 | 93 | 38 | 8 | 0 |
| Isoleucine (ppm) | 5 | 0 | 0 | 0 | 0 |
| Lysine (ppm) | 0 | 0 | 0 | 0 | 0 |
| Proline (ppm) | 650 | 387 | 102 | 25 | 0 |
| Total amount of amino acids (mass %) | 2.32 | 0.39 | 0.20 | 0.02 | 0.00 |
| 4-Aminobenzoic acid purity | ○ | ○ | ○ | ◎ | ◎ |
| Moisture-retaining property | ◎ | ◎ | ○ | ○ | X |
| Antibacterial property | ○ | ○ | ◎ | ◎ | ◎ |

Example VI

Example VI-1

<Production of 3,4-Dihydroxybenzoic Acid by Bioprocess>
A culture liquid obtained by a bioprocess that utilized a plant-derived saccharide and a microorganism was subjected to a concentration treatment by reduced pressure concentration so that the total solid content concentration would be 15% to 30% by mass. The degree of pressure reduction was set to 100 to 5000 Pa, the liquid temperature was set to 30°

C. to 80° C., and the concentration treatment was carried out by a reduced pressure distillation facility. Although the degree of concentration depends on the treatment time, a concentrated liquid having a total solid content concentration of 15% to 30% by mass was collected by the concentration treatment for 6 to 8 hours. Hydrochloric acid was added to this concentrated liquid to adjust the pH to be equal to or less than 4, and the mixture was further cooled to 0° C. to room temperature. A crystallization product was collected by filtration, washed appropriately, and then dried under reduced pressure, and high-purity 3,4-dihydroxybenzoic acid having a purity of equal to or more than 99% was collected.

The collected high-purity 3,4-dihydroxybenzoic acid, that is, the cyclic compound, did not include petroleum-derived impurities.

Example VI-2

<Production of Shikimic Acid by Bioprocess>

Activated carbon was added to a culture liquid obtained by a bioprocess that utilized a plant-derived saccharide and a microorganism, and the culture liquid was subjected to an activated carbon treatment. Next, a column packed with an ion exchange resin was prepared and treated with a 2 mol/L aqueous solution of sodium hydroxide. The ion exchange resin used is a strongly basic anion exchange resin. Pure water was passed through the column until the effluent water became neutral, subsequently the raw material liquid treated with activated carbon was passed through the column, and then pure water was passed therethrough. Then, a 2 mol/L aqueous solution of acetic acid was passed through as an eluent, and an acidic fraction was collected. The concentration of shikimic acid was measured for each of the collected fractions, and the eluent was passed through until the elution of shikimic acid was completed. A solid was precipitated by concentration and crystallization against the eluent, and solid shikimic acid was obtained. Concentration and crystallization is a treatment in which a concentration treatment and a cooled crystallization treatment are carried out in sequence to precipitate solid shikimic acid.

The collected high-purity shikimic acid, that is, the cyclic compound, did not include petroleum-derived impurities.

Example V

Example V-1

<Production of 3,4-Dihydroxybenzoic Acid by Bioprocess>

A culture liquid obtained by a bioprocess that utilized a plant-derived saccharide and a microorganism was subjected to a concentration treatment by reduced pressure concentration so that the total solid content concentration would be 15% to 30% by mass. The degree of pressure reduction was set to 100 to 5000 Pa, the liquid temperature was set to 30° C. to 80° C., and the concentration treatment was carried out by a reduced pressure distillation facility. Although the degree of concentration depends on the treatment time, a concentrated liquid having a total solid content concentration of 15% to 30% by mass was collected by the concentration treatment for 6 to 8 hours. Hydrochloric acid was added to this concentrated liquid to adjust the pH to be equal to or less than 4, and the mixture was further cooled to 0° C. to room temperature. A crystallization product was collected by filtration, washed appropriately, and then dried under reduced pressure, and high-purity 3,4-dihydroxybenzoic acid having a purity of equal to or more than 99% was collected.

The collected high-purity 3,4-dihydroxybenzoic acid, that is, the cyclic compound, did not include petroleum-derived impurities.

Example V-2

<Production of Shikimic Acid by Bioprocess>

Activated carbon was added to a culture liquid obtained by a bioprocess that utilized a plant-derived saccharide and a microorganism, and the culture liquid was subjected to an activated carbon treatment. Next, a column packed with an ion exchange resin was prepared and treated with a 2 mol/L aqueous solution of sodium hydroxide. The ion exchange resin used is a strongly basic anion exchange resin. Pure water was passed through the column until the effluent water became neutral, subsequently the raw material liquid treated with activated carbon was passed through the column, and then pure water was passed therethrough. Then, a 2 mol/L aqueous solution of acetic acid was passed through as an eluent, and an acidic fraction was collected. The concentration of shikimic acid was measured for each of the collected fractions, and the eluent was passed through until the elution of shikimic acid was completed. A solid was precipitated by concentration and crystallization against the eluent, and solid shikimic acid was obtained. Concentration and crystallization is a treatment in which a concentration treatment and a cooled crystallization treatment are carried out in sequence to precipitate solid shikimic acid.

The collected high-purity shikimic acid, that is, the cyclic compound, did not include petroleum-derived impurities.

This application claims priority from Japanese Patent Application No. 2019-064431, filed on Mar. 28, 2019; Japanese Patent Application No. 2019-064432, filed on Mar. 28, 2019; Japanese Patent Application No. 2019-066870, filed on Mar. 29, 2019; Japanese Patent Application No. 2019-066874, filed on Mar. 29, 2019; and Japanese Patent Application No. 2019-066883, filed on Mar. 29, 2019, the disclosures of which are incorporated herein by reference.

What is claim is:

1. A water-soluble additive composition comprising a cyclic carboxylic acid, wherein the water-soluble additive composition satisfies the following Conditions 1 or 2:
 (Condition 1) the following components (A) and (B1) are included:
 (A) the cyclic carboxylic acid, which is other than the following component (B1), and
 (B1) one or more selected from the group consisting of gallic acid and an ester thereof;
 wherein the cyclic carboxylic acid (A) is one or more selected from the group consisting of protocatechuic acid, shikimic acid, 4-hydroxybenzoic acid, and 4-aminobenzoic acid,
 the water-soluble additive composition of the Condition 1 is obtained by a bioprocess, and
 (Condition 2) a total content of $Na^+$ and $NH_4^+$ is equal to or more than 100 ppm and equal to or less than 5000 ppm with respect to the cyclic carboxylic acid.

2. The water-soluble additive composition according to claim 1, wherein the water-soluble additive composition satisfies the Condition 1 and is an antibacterial agent composition.

3. The water-soluble additive composition according to claim 2, wherein a content of the component (B1) with respect to a content of the component (A) ((B1)/(A)) in the antibacterial agent composition is equal to or more than 0.01 and equal to or less than 5 in a mass ratio.

4. The water-soluble additive composition according to claim 1,
wherein a content of the component (A) is equal to or more than 95% by mass and equal to or less than 99% by mass, and a content of the component (B1) is equal to or more than 1% by mass and equal to or less than 5% by mass, with respect to the total amount of the water-soluble additive composition.

5. The water-soluble additive composition according to claim 1, wherein the component (A) and the component (B1) are derived from a plant-derived saccharide and a microorganism.

6. The water-soluble additive composition according to claim 1, wherein the water-soluble additive composition satisfies the Condition 2.

7. The water-soluble additive composition according to claim 6, wherein the cyclic carboxylic acid is one or more selected from the group consisting of protocatechuic acid, shikimic acid, 4-hydroxybenzoic acid, 4-aminobenzoic acid, and ferulic acid.

8. The water-soluble additive composition according to claim 6, wherein a content of the cyclic carboxylic acid in the water-soluble additive composition is equal to or more than 95% by mass and equal to or less than 99.9% by mass with respect to a total amount of the water-soluble additive composition.

* * * * *